(12) United States Patent
Jain et al.

(10) Patent No.: US 8,722,715 B2
(45) Date of Patent: *May 13, 2014

(54) ANTIMICROBIAL OXAZOLIDINONE, HYDANTOIN AND IMIDAZOLIDINONE COMPOSITIONS

(75) Inventors: Rakesh K. Jain, Fremont, CA (US); Eddy Low, Foster City, CA (US); Charles Francavilla, Fremont, CA (US); Timothy P. Shiau, Oakland, CA (US); Bum Kim, Pleasanton, CA (US); Satheesh K. Nair, Emeryville, CA (US)

(73) Assignee: NovaBay Pharmaceuticals, Emeryville, CA (US)

( * ) Notice: Subject to any disclaimer, the term of this patent is extended or adjusted under 35 U.S.C. 154(b) by 857 days.

This patent is subject to a terminal disclaimer.

(21) Appl. No.: 12/612,572

(22) Filed: Nov. 4, 2009

(65) Prior Publication Data

US 2010/0137349 A1    Jun. 3, 2010

Related U.S. Application Data

(60) Provisional application No. 61/112,681, filed on Nov. 7, 2008.

(51) Int. Cl.
| | | |
|---|---|---|
| A61K 31/422 | (2006.01) | |
| A61K 31/4166 | (2006.01) | |
| A61K 31/4178 | (2006.01) | |
| C07D 233/02 | (2006.01) | |
| C07D 233/38 | (2006.01) | |
| C07D 233/80 | (2006.01) | |
| C07D 403/04 | (2006.01) | |
| C07D 263/10 | (2006.01) | |

(52) U.S. Cl.
USPC ........ 514/375; 514/376; 514/393; 548/314.7; 548/316.7; 548/229; 548/232; 548/320.1

(58) Field of Classification Search
None
See application file for complete search history.

(56) References Cited

U.S. PATENT DOCUMENTS

| | | | |
|---|---|---|---|
| 2,798,875 A * | 7/1957 | Scheer Walter E et al. .......................... | 548/319.5 |
| 2,945,045 A * | 7/1960 | Frank Levy M et al. .. | 548/319.1 |
| 3,591,601 A | 7/1971 | Walles | |
| 3,931,213 A | 1/1976 | Kaminski et al. | |
| 4,000,293 A | 12/1976 | Kaminski et al. | |
| 4,049,818 A * | 9/1977 | Bodor et al. .................. | 514/278 |
| 5,126,057 A | 6/1992 | Worley et al. | |
| 5,162,354 A | 11/1992 | Fernando Del Corral et al. | |
| 6,162,487 A * | 12/2000 | Darouiche .................... | 427/2.14 |
| 7,173,073 B2 | 2/2007 | Rathore | |
| 7,335,373 B2 | 2/2008 | Worley et al. | |
| 7,846,971 B2 | 12/2010 | Najafi et al. | |
| 7,893,109 B2 | 2/2011 | Bassiri et al. | |
| 2004/0043914 A1 * | 3/2004 | Kaziska et al. ................ | 510/383 |
| 2008/0226618 A1 * | 9/2008 | Mansoor et al. ........... | 424/130.1 |

OTHER PUBLICATIONS

Nagl, M., Gruber, A., Fuchs, A., Lell, C. P., Lemberger, E.-M., Borg-von Zepelin, M., Wurzner, R., Impact of N-Chlorotaurine on Viability and Production of Secreted Aspartyl Proteinases of Candida spp. Antimicrobial Agents and Chemotherapy. Jun. 2002, 46, 1996-1999.*
Nagl, M., Hess, M. W., Pfaller, K., Hengster, P., Cottardi, W., Bactericidal Activity of Micromolar N-Chlorotaurine: Evidence for Its Antimicrobial Function in the Human Defense System. Antimicrobial Agents and Chemotherapy. Sep. 2000, 55, 2507-2513.*
Williams, D. E., Worley, S. D., Wheatley, W. B., Swango, L. J., Bactericidal Properties of a New Water Disinfectant. Applied and Environmental Microbiology. Mar. 1985. 49, 637-643.*
McMurry, J. Organic Chemistry. 5th ed. Pacific Grove, CA: Brookes/Cole, 2000. Jan. 1284. Print.*
McDonnell et al., Antiseptics and Disinfectants: Activity, Action, and Resistance. Clinical Microbiology Review, 1999, 12, 147-179.*
Ito et al., A medium-term rat liver bioassay for rapid in vivo detection of carcinogenic potential of chemicals, 2003, 94, 3-8.*
Selk, Pogany & Higuchi, "Comparative Antimicrobial Activity, In Vitro and In Vivo, of Soft N-Chloramine Systems and Chlorhexidine," Applied and Environmental Microbiology, Apr. 1982, p. 899-904 vol. 43, No. 4 (US).
Williams, Worley, Wheatly & Swango, "Bactericidal Properties of a New Water Disinfectant," Applied and Environmental Microbiology, Mar. 1985, p. 637-643 vol. 49, No. 3 (American Society for Microbiology) (US).

* cited by examiner

Primary Examiner — Michael Barker
Assistant Examiner — Po-Chih Chen
(74) Attorney, Agent, or Firm — Sam L. Nguyen

(57) ABSTRACT

The present application relates to N-chlorinated oxazolidinone, hydantoin and imidazolidinone compounds of Formula I

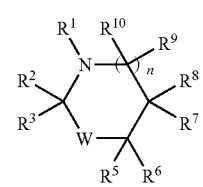

or pharmaceutically acceptable salts thereof, and associated compositions and methods of use as antimicrobial agents.

17 Claims, No Drawings

ANTIMICROBIAL OXAZOLIDINONE, HYDANTOIN AND IMIDAZOLIDINONE COMPOSITIONS

RELATED APPLICATIONS

This application claims the benefit of U.S. Provisional Application No. 61/112,681, filed on Nov. 7, 2008, which is incorporated by reference herein in its entirety.

FIELD

The present application relates to N-chlorinated oxazolidinone, hydantoin and imidazolidinone compounds, and associated compositions and methods of use as antimicrobial agents.

BACKGROUND

Halogens and halogenating agents have long been used as disinfectants, antiseptics and antimicrobials [see, e.g., G. F. Connell, *The Chlorination/Chloramination Handbook*, Am. Water Works Assn. (1996); H. W. Banks, U.S. Pat. No. 1,813, 109; and F. C. Schmelkes, U.S. Pat. No. 1,958,370]. While effectively killing bacteria, fungi and viruses, many chlorinating agents are also toxic to mammalian cells [see, e.g., I. U. Schraufstatter et al., *J. Clin. Invest.* 85, 554-562 (1990)], which can limit their use in therapeutic applications.

Organic N-chloramine carboxylic acids have been proposed as mild antimicrobials (S. A. Pogany et al., U.S. Pat. No. 4,386,103) and as drugs acting on the central nervous system (N. M. van Gelder et al., U.S. Pat. No. 6,451,761). Certain antimicrobial N-halogenated heterocyclic compounds are also known. For example, J. J. Kaminski et al. (U.S. Pat. Nos. 3,931,213 and 4,000,493) disclose various antibacterial 3-chloro-2-oxazolidinones; S. D. Worley et al. (U.S. Pat. No. 5,126,057) discloses biocidal N-halo derivatives of substituted imidazolidin-4-one compounds; Fernando Del Corral et al. (U.S. Pat. No. 5,162,354) describes 3-halo-5-halomethyl-2-oxazolidinones as microbicidal compounds; O. Rathore (U.S. Pat. No. 7,173,073) discloses ophthalmic devices containing N-chlorinated or N-brominated heterocyclic groups; and S. D. Worley et al. (U.S. Pat. No. 7,335,373) discloses biocidal siloxane coating material containing N-halogenated amine and amide functional groups. Also, A. J. Kaziska et al. (U.S. Pub. No. 2004/0043914 A1), M. F. Czuczak et al. (U.S. Pub. No. 2003/0104965 A1), Y. Nobata and Z. Yamaguchi (Japanese Pub. No. JP/2003/104806 A), T. Nakai and K. Ito (Japanese Pub. No. JP/2003/104805 A), and Y. Murata (Japanese Pub. No. JP/2004/203779 A) disclose compositions of, and sanitizing methods using, various partially halogenated hydantoin compounds.

Despite these known compounds, additional compounds with favorable antimicrobial, stability, water solubility, toxicity, and other properties, are still needed.

SUMMARY

The present application describes compounds useful as antimicrobial agents, including as antibacterial, anti-infective, disinfectant, antifungal, germicidal or antiviral agents.

Compounds of this application are represented by the following general structure:

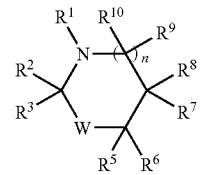

or a salt thereof, wherein:
n is 0 or 1;
W is $NR^4$, O, S, S($=$O) or S($=$O)$_2$;
$R^1$ is H, Cl, Br, -L-X or optionally substituted alkyl or heteroalkyl;
$R^2$ and $R^3$ are each independently H, -L-X, or optionally substituted alkyl or heteroalkyl, or $R^2$ and $R^3$ together with the carbon to which they are attached form a carbonyl, -L-X, or an optionally substituted cycloalkyl or heterocycloalkyl group;
$R^4$ is H, Cl, Br, -L-X or optionally substituted alkyl or heteroalkyl;
$R^5$ and $R^6$ are each independently H, -L-X or optionally substituted alkyl or heteroalkyl; or $R^5$ and $R^6$ together with the carbon to which they are attached form a carbonyl, -L-X or an optionally substituted cycloalkyl or heterocycloalkyl group;
$R^7$ and $R^8$ are each independently H, -L-X or optionally substituted alkyl or heteroalkyl; or $R^7$ and $R^8$ together with the carbon to which they are attached form a carbonyl, -L-X or an optionally substituted cycloalkyl or heterocycloalkyl group;
$R^9$ and $R^{10}$ are each independently H, -L-X or optionally substituted alkyl or heteroalkyl; or $R^9$ and $R^{10}$ together with the carbon to which they are attached form a carbonyl, -L-X or an optionally substituted cycloalkyl or heterocycloalkyl group;
each L is independently an optionally substituted $C_{1-6}$ alkyl, heteroalkyl, cycloalkyl or heterocycloalkyl group; and
each X is independently —$SO_3H$, —$N^+R^aR^bR^c$, —$B(OH)_2$, —$CO_2H$, —$PO_3H_2$ or —$PO_3HR^a$ and $R^a$, $R^b$, and/or $R^c$ are independently a bond or an optionally substituted alkyl or heteroalkyl groups, or may form, together with the N to which they are attached, a heterocycloalkyl group
with the provisos that:
at least one of $R^1$, $R^2$, $R^3$, $R^4$, $R^5$, $R^6$, $R^7$, $R^8$, $R^9$ or $R^{10}$ is -L-X; and
at least one of $R^2$ and $R^3$, $R^5$ and $R^6$, or $R^7$ and $R^8$, together with the carbon to which they are attached, form a carbonyl; provided that (i) $R^5$, $R^6$ and the carbon to which they are attached, and $R^7$, $R^8$ and the carbon to which they are attached, are not both carbonyl; and (ii) $R^7$, $R^8$ and the carbon to which they are attached, and $R^9$, $R^{10}$ and the carbon to which they are attached, are not both carbonyl.

Processes useful for the preparation of the compounds, compositions comprising the compounds, methods for the prevention or treatment of microbial infections (including bacterial, fungal and viral infections) using the compounds and compositions of the disclosure are described. Method of using these compounds and compositions in treating, disinfecting, decontaminating, or cleaning surfaces or areas such as of medical devices, instruments, tools, and the like, are also described.

DETAILED DESCRIPTION

This application is not limited to particular methodologies (e.g., modes of administration) or the specific compositions described, as such may, vary. It is also to be understood that the terminology used herein is for the purpose of describing particular embodiments only, and is not intended to be limiting, since the scope of the present application will be limited only by the appended claims and their equivalents.

Unless defined otherwise, all technical and scientific terms used herein have the same meaning as commonly understood by one of ordinary skill in the art to which this application belongs. It must be noted that as used herein and in the appended claims, the singular forms "a", "and", and "the" include plural referents unless the context clearly dictates otherwise. Thus, e.g., reference to "the compound" includes a plurality of such compounds and reference to "the assay" includes reference to one or more assays and equivalents thereof known to those skilled in the art, and so forth. Also, a divalent group, such as a divalent "alkyl" group, a divalent "aryl" group, etc., may also be referred to as an "alkylene" group or an "alkylenyl" group, an "arylene" group or an "arylenyl" group, respectively.

As utilized in accordance with the present disclosure, the following terms, unless otherwise indicated, shall be understood to have the following meanings:

"Alkyl" refers to a saturated, branched, or straight-chain hydrocarbon radical derived by the removal of one hydrogen atom from a single carbon atom of a parent alkane. Alkyl groups include, but are not limited to, methyl; ethyl; propyls such as propan-1-yl, propan-2-yl (iso-propyl), cyclopropan-1-yl, etc.; butyls such as butan-1-yl, butan-2-yl (sec-butyl), 2-methyl-propan-1-yl (iso-butyl), 2-methyl-propan-2-yl (t-butyl), cyclobutan-1-yl; pentyls; hexyls; octyls; dodecyls; octadecyls; and the like. An alkyl group comprises from 1 to about 22 carbon atoms, e.g., from 1 to 22 carbon atoms, e.g. from 1 to 12 carbon atoms, or, e.g., from 1 to 6 carbon atoms.

"Alkylcycloalkyl" refers to an alkyl group attached to a cycloalkyl group. Alkylcycloalkyl groups include, but are not limited to, methyl cyclopentyl, methyl cyclobutyl, ethyl cyclohexyl, and the like. An alkylcycloalkyl group comprises from 4 to about 32 carbon atoms, i.e. the alkyl group can comprise from 1 to about 22 carbon atoms and the cycloalkyl group can comprise from 3 to about 10 carbon atoms.

"Active ingredient" refers to a compound of Formula I, or a salt thereof.

"Acyl" refers to a radical —C(=O)R, where R is hydrogen, alkyl, cycloalkyl, cycloheteroalkyl, aryl, arylalkyl, heteroalkyl, heteroaryl or heteroarylalkyl as defined herein, each of which may be optionally substituted, as defined herein. Representative examples include, but are not limited to formyl, acetyl, cylcohexylcarbonyl, cyclohexylmethylcarbonyl, benzoyl, benzylcarbonyl and the like.

"Acylamino" (or alternatively "acylamido") refers to a radical —NR'C(=O)R, where R' and R are each independently hydrogen, alkyl, cycloalkyl, cycloheteroalkyl, aryl, arylalkyl, heteroalkyl, heteroaryl or heteroarylalkyl, as defined herein, each of which may be optionally substituted, as defined herein. Representative examples include, but are not limited to, formylamino, acetylamino (i.e., acetamido), cyclohexylcarbonylamino, cyclohexylmethyl-carbonylamino, benzoylamino (i.e., benzamido), benzylcarbonylamino and the like.

"Acyloxy" refers to a radical —OC(=O)R, where R is hydrogen, alkyl, cycloalkyl, cycloheteroalkyl, aryl, arylalkyl, heteroalkyl, heteroaryl or heteroarylalkyl, as defined herein, each of which may be optionally substituted, as defined herein. Representative examples include, but are not limited to, acetyloxy (or acetoxy), butanoyloxy, benzoyloxy and the like.

"Alkoxy" refers to a radical —OR where R represents an alkyl or cycloalkyl group as defined herein, each of which may be optionally substituted, as defined herein. Representative examples include, but are not limited to, methoxy, ethoxy, propoxy, butoxy, cyclohexyloxy and the like.

"Alkoxycarbonyl" refers to a radical —C(=O)-alkoxy where alkoxy is as defined herein.

"Alkylsulfonyl" refers to a radical —S(=O)$_2$R where R is an alkyl or cycloalkyl group as defined herein, each of which may be optionally substituted, as defined herein. Representative examples include, but are not limited to, methylsulfonyl, ethylsulfonyl, propylsulfonyl, butylsulfonyl and the like.

"Aryl" refers to an aromatic hydrocarbon group which may be a single aromatic ring or multiple aromatic rings which are fused together, linked covalently, or linked to a common group such as a methylene or ethylene moiety. Aryl groups include, but are not limited to, groups derived from acenaphthylene, anthracene, azulene, benzene, biphenyl, chrysene, cyclopentadiene, diphenylmethyl, fluoranthene, fluorene, indane, indene, naphthalene, pentalene, perylene, phenalene, phenanthrene, pyrene, triphenylene, and the like. An aryl group comprises from 5 to about 20 carbon atoms, e.g., from 6 to 20 carbon atoms, e.g. from 5 to 10 carbon atoms.

"Arylalkyl" refers to an aryl group attached to an alkyl group. Arylalkyl groups include, but are not limited to, benzyl, 2-phenylethan-1-yl, 2-phenylethen-1-yl, naphthylmethyl, 2-naphthylethan-1-yl, 2-naphthylethen-1-yl, naphthobenzyl, 2-naphthophenylethan-1-yl and the like. Where specific alkyl moieties are intended, the nomenclature arylalkanyl, arylalkenyl and/or arylalkynyl may be used. An arylalkyl group comprises from 7 to about 42 carbon atoms, e.g. the alkyl group can comprise from 1 to about 22 carbon atoms and the aryl group can comprise from 6 to about 20 carbon atoms.

"Carbamoyl" refers to the radical —OC(=O)N(R)$_2$ where each R group is independently hydrogen, alkyl, cycloalkyl or aryl as defined herein, which may be optionally substituted, as defined herein.

"Carbonate" refers to the group —OCO$_2^-$.

"Compounds" as used herein refers to any of the compounds encompassed by Formula I as disclosed herein. The compounds may be neutral, charged (e.g. cationic or anionic), or in a salt form. The compounds may be identified by structure or by name. If the chemical structure and chemical name conflict, the chemical structure will be determinative of the identity of the compound. The compounds may contain one or more chiral centers and/or double bonds and therefore, may exist as stereoisomers, such as double-bond isomers (i.e., geometric isomers), enantiomers or diastereomers. Accordingly, when stereochemistry at chiral centers is not specified, the chemical structures depicted herein encompass all possible configurations at those chiral centers including the stereoisomerically pure form (e.g., geometrically pure, enantiomerically pure or diastereomerically pure) and enantiomeric and stereoisomeric mixtures. Enantiomeric and stereoisomeric mixtures can be resolved into their component enantiomers or stereoisomers using separation techniques or chiral synthesis techniques well known to the skilled artisan. The compounds may also exist in several tautomeric forms including the enol form, the keto form and mixtures thereof. Accordingly, the chemical structures depicted herein encompass all possible tautomeric forms of the illustrated compounds. The compounds also include isotopically labeled compounds where one or more atoms have an atomic mass different from the atomic mass conventionally found in nature. Examples of isotopes that may be incorporated into the compounds include, but are not limited to, $^2$H, $^3$H, $^{13}$C, $^{14}$C, $^{15}$N, $^{17}$O, $^{18}$O, $^{18}$F, $^{31}$P, $^{32}$P, $^{35}$S and $^{36}$Cl. Compounds may exist in unsolvated forms as well as solvated forms, including hydrated forms and as N-oxides. In general, the neutral, charged, protonated, salt, hydrated, solvated and N-oxide forms are within the scope of the present disclosure.

"Cycloalkyl" refers to a saturated or unsaturated cyclic alkyl radical. Typical cycloalkyl groups include, but are not limited to, groups derived from cyclopropane, cyclobutane, cyclopentane, cyclohexane, cyclohexene, 1,3-cyclohexadiene, and the like. A cycloalkyl group comprises from 3 to about 10 carbon atoms, e.g. from 3 to 10 carbon atoms, or, e.g. from 3 to 6 carbon atoms.

"Effective amount" means the amount of a compound that, when administered to a subject, surface or area for treating or preventing a microbial infection or contamination, is sufficient to effect such treatment or prevention. The "effective amount" will vary depending on the compound, the severity of the condition causing the microbial infection and the age, weight, etc., of the subject to be treated.

"Electron-withdrawing group" refers to atoms or functional groups which are electronegative either through a resonance effect or an inductive effect. Examples of such atoms and functional groups include, but are not limited to —CO$_2$R$^o$, —CO—, —NO$_2$, —SO$_3$R$^o$, cyano, halogen (F, Cl, Br, I), and haloalkyl (e.g. —CF$_3$), where R$^o$ is H, alkyl, aryl, cycloalkyl, heteroalkyl, heteroaryl or cycloheteroalkyl group, as defined herein, each of which may be optionally and independently substituted.

"Halide" means a halogen bearing a negative charge, including fluoride, chloride, bromide, and iodide.

"Halo" means a halogen, including fluoro, chloro, bromo, and iodo.

"Heteroalkyl" refers to an alkyl radical in which one or more of the carbon atoms (and any associated hydrogen atoms) are each independently replaced with the same or different heteroatomic groups. Heteroatomic groups include, but are not limited to, —NR$^o$—, —O—, —S—, —PH—, —P(O)$_2$—, —S(O)—, —S(O)$_2$—, and the like, where R$^o$ is defined above. Heteroalkyl groups include, but are not limited to, —O—CH$_3$, —CH$_2$—O—CH$_3$, —S—CH$_3$, —CH$_2$—S—CH$_3$, —NR$^o$—CH$_3$, —CH$_2$—NR$^{oo}$—CH$_3$, and the like, where R$^o$ and R$^{oo}$ are defined above. A heteroalkyl group can comprise from 1 to about 22 carbon and hetero atoms, e.g., from 1 to 22 carbon and heteroatoms, e.g. from 1 to 12 carbon and hetero atoms, e.g., from 1 to 6 carbon and hetero atoms.

"Heteroaryl" refers to an aryl group in which one or more of the carbon atoms (and any associated hydrogen atoms) are each independently replaced with the same or different heteroatomic groups. Typical heteroatomic groups include, but are not limited to, —N—, —O—, —S—, and —NR$^o$—, where R$^o$ is defined above. Typical heteroaryl groups include, but are not limited to, groups derived from acridine, carbazole, carboline, cinnoline, furan, imidazole, indazole, indole, indoline, indolizine, isobenzofuran, isochromene, isoindole, isoindoline, isoquinoline, isothiazole, isoxazole, naphthyridine, oxadiazole, oxazole, perimidine, phenanthridine, phenanthroline, phenazine, phthalazine, pteridine, purine, pyran, pyrazine, pyrazole, pyridazine, pyridine, pyrimidine, pyrrole, pyrrolizine, quinazoline, quinoline, quinolizine, quinoxaline, tetrazole, thiadiazole, thiazole, thiophene, triazole, xanthene, and the like. A heteroaryl group comprises from 5 to about 20 atoms, e.g., from 5 to 20 atoms, e.g. from 5 to 10 atoms.

"Heterocycloalkyl" refers to a saturated or unsaturated cycloalkyl radical in which one or more carbon atoms (and any associated hydrogen atoms) are independently replaced with the same or different heteroatom. Typical heteroatoms to replace the carbon atom(s) include, but are not limited to, N, P, O, S, etc. A heterocycloalkyl group may also contain a charged heteroatom or group, e.g., a quaternized ammonium group such as —N$^+$(R)$_2$— wherein R is alkyl, e.g., methyl, ethyl, etc. Heterocycloalkyl groups include, but are not limited to, groups derived from epoxides, imidazolidine, morpholine, piperazine, piperidine, pyrazolidine, piperidine, pyrrolidine, quinuclidine, N-bromopyrrolidine, N-bromopiperidine, N-chloropyrrolidine, N-chloropiperidine, an N,N-dialkylpyrrolidinium, such as N,N-dimethylpyrrolidinium, a N,N-dialkylpiperidinium such as N,N-dimethylpiperidium, and the like. The heterocycloalkyl group comprises from 3 to about 10 carbon and hetero atoms in the ring.

"Microbial" refers to bacteria, fungi (including, e.g., yeast) or virus, and any associated biofilm.

"Pharmaceutically acceptable" refers to that which is useful in preparing a pharmaceutical composition that is generally safe, non-toxic, and neither biologically nor otherwise undesirable, and includes that which is acceptable for veterinary as well as human pharmaceutical use.

"Pharmaceutically acceptable salt" refers to a salt of a compound that is pharmaceutically acceptable and that possesses (or can be converted to a form that possesses) the desired pharmacological activity of the parent compound. Such salts include acid addition salts formed with inorganic acids such as hydrochloric acid, hydrobromic acid, sulfuric acid, nitric acid, phosphoric acid, and the like; or formed with organic acids such as acetic acid, benzenesulfonic acid, benzoic acid, camphorsulfonic acid, citric acid, ethanesulfonic acid, fumaric acid, glucoheptonic acid, gluconic acid, lactic acid, maleic acid, malonic acid, mandelic acid, methanesulfonic acid, 2-napththalenesulfonic acid, oleic acid, palmitic acid, propionic acid, stearic acid, succinic acid, tartaric acid, p-toluenesulfonic acid, trimethylacetic acid, and the like, and salts formed when an acidic proton present in the parent compound is replaced by either a metal ion, e.g., an alkali metal ion, an alkaline earth ion, or an aluminum ion; or coordinates with an organic base such as diethanolamine, triethanolamine, N-methylglucamine and the like. Also included in this definition are ammonium and substituted or quaternized ammonium salts. Representative non-limiting lists of pharmaceutically acceptable salts can be found in S. M. Berge et al., *J. Pharma Sci.,* 66(1), 1-19 (1977), and *Remington: The Science and Practice of Pharmacy,* R. Hendrickson, ed., 21st edition, Lippincott, Williams & Wilkins, Philadelphia, Pa., (2005), at p. 732, Table 38-5, both of which are hereby incorporated by reference herein.

"Pharmaceutically acceptable carrier" refers to a pharmaceutically acceptable diluent, adjuvant, excipient or vehicle and the like with which a compound is combined and/or administered.

"Pharmaceutical composition" as used herein comprises one or more compounds of Formula I and a pharmaceutically acceptable carrier.

"Phosphate" refers to the group (R)$_n$PO$_4^{3-n)-}$ where n is 0, 1 or 2 and R can be hydrogen, alkyl, aryl, cycloalkyl, heteroalkyl, or heteroaryl as defined herein, each of which may be optionally substituted.

"Prevent", "preventing" and "prevention" of a microbial infection refer to reducing the risk of a subject from developing a microbial infection, or reducing the frequency or severity of a microbial infection in a subject.

"Protecting group" refers to a group of atoms that when attached to a reactive functional group in a molecule masks, reduces or prevents reactivity of the functional group. Examples of protecting groups can be found in P. G. M. Wuts and T. W. Greene, *Greene's Protective Groups in Organic*

*Synthesis* (4th Ed.), Wiley-Interscience, (2006), and Harrison et al., *Compendium of Synthetic Organic Methods*, Vols. 1-8 (John Wiley and Sons, 1971-1996). For example, representative amino protecting groups include, but are not limited to, formyl, acetyl, trifluoroacetyl, benzyl, benzyloxycarbonyl ("CBZ", "Cbz"), tert-butoxycarbonyl ("Boc"), trimethylsilyl ("TMS"), 2-trimethylsilyl-ethanesulfonyl ("SES"), trityl and substituted trityl groups, allyloxycarbonyl, 9-fluorenylmethyloxycarbonyl ("FMOC"), nitro-veratryloxycarbonyl ("NVOC") and the like. Representative hydroxy protecting groups include, but are not limited to, those where the hydroxy group is either acylated or alkylated such as benzyl, and trityl ethers as well as alkyl ethers, tetrahydropyranyl ethers, trialkylsilyl ethers and allyl ethers.

"Salt" refers to a cation coupled with an anion, either in solution or as a solid. Salts include pharmaceutically acceptable salts as well as solvent addition forms (solvates) of the same salt.

"Subject" refers to an animal (including, but not limited to, a bull, steer, cow, horse, bird, reptile, monotreme, dog, cat, etc.), including a human.

"Sulfate" refers to the group $SO_4^{-2}$.

"Substituted" refers to a group wherein one or more hydrogens (e.g., from 1 to 5, e.g., from 1 to 3) have been replaced with one or more substituents including, but not limited to, acylamino, alkoxy, alkyl, amino, amidino, aryl, carboxyl, carbamoyl, cyano, cycloalkyl, guanidino, halo, heteroalkyl, heteroaryl, heterocycloalkyl, hydroxyl, imidino, imino, nitro, oxamidino, oxo, methoxamidino, sulfonamido, thio, thioamido, any electron-withdrawing group, or a combination thereof.

"Treat", "treating" and "treatment" of a microbial infection or contamination refer to reducing the frequency or severity of symptoms of a microbial infection (including eliminating them), or avoiding or reducing the chances of the occurrence of a microbial infection, or killing or inhibiting the growth of bacteria, fungus or virus.

The following abbreviations may also be used: APCI: atmospheric pressure chemical ionization; Boc$_2$O: di-tert-butyl dicarbonate; Cmpd: compound; DCM: dichloromethane; DIEA: diisopropylethylamine; DMF: N,N-dimethylformamide; EDT: ethanedithiol; ESI: electrospray ionization; EtOAc: ethyl acetate; EtOH: ethanol; h: hour; HPLC: high pressure liquid chromatography; LCMS: high pressure liquid chromatography with mass spectrometer detector; MeOH: methanol; m/z: mass to charge ratio; NMR: nuclear magnetic resonance; pos: positive; PTFE: polytetrafluoroethylene; RT or rt: room temperature; sat.: saturated; TFA: trifluoroacetic acid; TLC: thin layer chromatography. Other abbreviations commonly used in the art may also be used.

One aspect of the current disclosure relates to compounds of Formula I

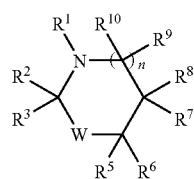

I or a salt thereof, wherein:
  n is 0 or 1;
  W is NR$^4$, O, S, S(=O) or S(=O)$_2$;

R$^1$ is H, Cl, Br, -L-X or optionally substituted alkyl or heteroalkyl;
  R$^2$ and R$^3$ are each independently H, -L-X, or optionally substituted alkyl or heteroalkyl, or R$^2$ and R$^3$ together with the carbon to which they are attached form a carbonyl, -L-X or an optionally substituted cycloalkyl or heterocycloalkyl group;
  R$^4$ is H, Cl, Br, -L-X or optionally substituted alkyl or heteroalkyl;
  R$^5$ and R$^6$ are each independently H, -L-X or optionally substituted alkyl or heteroalkyl; or R$^5$ and R$^6$ together with the carbon to which they are attached form a carbonyl, -L-X or an optionally substituted cycloalkyl or heterocycloalkyl group;
  R$^7$ and R$^8$ are each independently H, -L-X or optionally substituted alkyl or heteroalkyl; or R$^7$ and R$^8$ together with the carbon to which they are attached form a carbonyl, -L-X or an optionally substituted cycloalkyl or heterocycloalkyl group;
  R$^9$ and R$^{10}$ are each independently H, -L-X or optionally substituted alkyl or heteroalkyl; or R$^9$ and R$^{10}$ together with the carbon to which they are attached form a carbonyl, -L-X or an optionally substituted cycloalkyl or heterocycloalkyl group;
  each L is independently an optionally substituted $C_{1-6}$ alkyl, heteroalkyl, cycloalkyl or heterocycloalkyl group; and
  each X is independently —SO$_3$H, —N$^+$R$^a$R$^b$R$^c$, —B(OH)$_2$, —CO$_2$H, —PO$_3$H$_2$ or —PO$_3$HR$^a$ and R$^a$, R$^b$, and/or R$^c$ are independently a bond or an optionally substituted alkyl or heteroalkyl groups, or may form, together with the N to which they are attached, a heterocycloalkyl group;
  with the provisos that:
    at least one of R$^1$, R$^2$, R$^3$, R$^4$, R$^5$, R$^6$, R$^7$, R$^8$, R$^9$ or R$^{10}$ is -L-X; and
    at least one of R$^2$ and R$^3$, R$^5$ and R$^6$, or R$^7$ and R$^8$, together with the carbon to which they are attached, form a carbonyl; provided that (i) R$^5$, R$^6$ and the carbon to which they are attached, and R$^7$, R$^8$ and the carbon to which they are attached, are not both carbonyl; and (ii) R$^7$, R$^8$ and the carbon to which they are attached, and R$^9$, R$^{10}$ and the carbon to which they are attached, are not both carbonyl.

In certain compounds of Formula I, n is 0. For clarity, in these compounds, R$^9$ and R$^{10}$ are absent.

In certain compounds of Formula I, W is NR$^4$ or O.

In certain compounds of Formula I, R$^1$ and R$^4$ are not both H. In certain compounds of Formula I, at least one of either R$^1$ or R$^4$ is independently Cl or Br.

In certain compounds of Formula I, R$^1$ is Cl.

In certain compounds of Formula I, R$^4$ is Cl. In other compounds of Formula I, R$^4$ is alkyl. In yet other compounds of Formula I, R$^4$ is -L-X.

In certain compounds of Formula I, R$^2$, R$^3$ and the carbon to which they are attached; R$^5$, R$^6$ and the carbon to which they are attached; R$^7$, R$^8$ and the carbon to which they are attached; and/or R$^9$, R$^{10}$ and the carbon to which they are attached, independently form an optionally substituted cycloalkyl or heterocycloalkyl group. In such cases, the resulting compounds may be Spiro compounds. For example, in certain compounds of Formula I, R$^2$ and R$^3$, R$^5$ and R$^6$, Wand R$^8$, and/or R$^9$ and R$^{10}$, and the carbon to which they are attached, can be a N,N-dimethylpyrrolidinium or N,N-dimethylpiperidinium group (in which case the compound may be referred to as a Spiro compound). For clarity, in these compounds, R$^2$ and R$^3$, R$^5$ and R$^6$, Wand R$^8$ and/or R$^9$ and R$^{10}$ are considered to be -L-X, as illustrated by the following nonlimiting example:

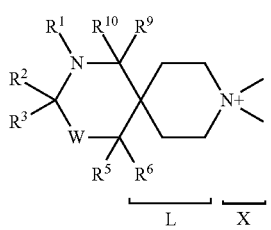

In certain compounds of Formula I, L is a $C_{1-6}$ alkyl group. For example, in certain compounds, L can be —$CH_2$—, —($CH_2$—$CH_2$)— or —($CH_2$)$_3$—. In other compounds of Formula I, L is a $C_{1-6}$ alkyl group wherein one or more of the carbon atoms is replaced with —O—, —$CF_2$—, —CHF—, —C($CF_3$)H—, —C(=O)—, —C(=O)O—, —OC(=O)—, —C(=O)$NR^d$—, —$NR^d$C(=O)—, —P(=O)($OR^e$)O—, —OP(=O)($OR^e$)—, —P(=O)($OR^e$)$NR^f$—, —$NR^f$P(=O)($OR^e$)—, —S(=O)$_2$—, —S(=O)$_2$O—, —OS(=O)$_2$—, —S(=O)$_2$$NR^g$—, —$NR^g$S(=O)$_2$—, or heteroaryl; and $R^d$, $R^e$, $R^f$ and $R^g$ are each independently selected from the group consisting of hydrogen, alkyl, aryl, cycloalkyl, heteroalkyl, heteroaryl and heterocycloalkyl, each of which may be optionally and independently substituted.

In certain compounds of Formula I, X is —$SO_3$H or —$N^+R^aR^bR^c$.

In certain compounds of Formula I, $R^a$, $R^b$, and $R^c$ are independently optionally substituted alkyl. For example, in certain compounds of Formula I, $R^a$, $R^b$ and $R^c$ are methyl. In other compounds of Formula I, $R^a$ may be alkyl (e.g. methyl) and $R^b$ and $R^c$ together with the N to which they are attached may form a pyrrolidinium group.

In certain compounds of Formula I, the compound is an acid, e.g. a sulfonic acid. In other compounds of Formula I, the compound is a salt, e.g. a pharmaceutically acceptable salt. For example, a compound of Formula I may be a sodium, chloride, dichloride, acetate, ammonium, or substituted or quaternary ammonium salt.

Another aspect of the current disclosure relates to compounds of Formula IA

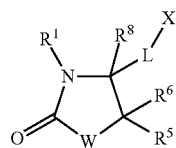

or a salt thereof, wherein:
W is $NR^4$ or O;
$R^1$ is H, Cl, Br or optionally substituted alkyl or heteroalkyl;
$R^4$ is H, Cl, Br or optionally substituted alkyl or heteroalkyl, with the proviso that $R^1$ and $R^4$ are not both H;
$R^5$ and $R^6$ are each independently H or optionally substituted alkyl or heteroalkyl; or $R^5$ and $R^6$ together with the carbon to which they are attached form a carbonyl or an optionally substituted cycloalkyl or heterocycloalkyl;
$R^8$ is H, optionally substituted alkyl or heteroalkyl, or -L-X;
each L is independently an optionally substituted $C_{1-6}$ alkyl, heteroalkyl, cycloalkyl or heterocycloalkyl group; and
each X is independently —$SO_3$H, —$N^+R^aR^bR^c$, —B(OH)$_2$, —$CO_2$H, —$PO_3H_2$ or —$PO_3HR^a$ and $R^a$, $R^b$, and/or $R^c$ are independently and optionally substituted alkyl, heteroalkyl, groups, or may form, together with the N to which they are attached, a heterocycloalkyl group.

In certain compounds of Formula IA, $R^1$ is Cl.
In certain compounds of Formula IA, W is O.
In certain compounds of Formula IA, $R^5$ and $R^6$ are H. In other compounds of Formula IA, $R^5$ and $R^6$ are alkyl.
In certain compounds of Formula IA, $R^8$ is H or alkyl. In other compounds of Formula IA, $R^8$ is -L-X.
In certain compounds of Formula IA, each X is $SO_3$H. In other compounds of Formula IA, each X is —$N^+R^aR^bR^c$, wherein $R^a$, $R^b$ and $R^c$ are optionally and independently substituted alkyl and heteroalkyl groups. In certain of these compounds, $R^a$, $R^b$ and $R^c$ is methyl. In other compounds of Formula IA, one X can be —$SO_3$H and another X can be —$N^+R^aR^bR^c$ as described above.

In certain compounds of Formula IA, each L is —($CH_2$)—. In other compounds of Formula IA, each L is —($CH_2$—$CH_2$)— or —($CH_2$)$_3$—.

Another aspect of the current disclosure relates to compounds of Formula IB

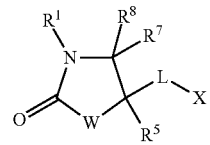

or a salt thereof, wherein:
W is $NR^4$ or O;
$R^1$ is H, Cl, Br or optionally substituted alkyl or heteroalkyl;
$R^4$ is H, Cl, Br or optionally substituted alkyl or heteroalkyl, with the proviso that $R^1$ and $R^4$ are not both H;
$R^5$ is H, optionally substituted alkyl or heteroalkyl or -L-X;
$R^7$ and $R^8$ are each independently H or optionally substituted alkyl or heteroalkyl; or $R^7$ and $R^8$ together with the carbon to which they are attached form a carbonyl or an optionally substituted cycloalkyl or heterocycloalkyl;
each L is independently an optionally substituted $C_{1-6}$ alkyl, heteroalkyl, cycloalkyl or heterocycloalkyl group; and
each X is independently —$SO_3$H, —$N^+R^aR^bR^c$, —B(OH)$_2$, —$CO_2$H, —$PO_3H_2$ or —$PO_3HR^a$ and $R^a$, $R^b$, and/or $R^c$ are independently and optionally substituted alkyl, heteroalkyl, groups, or may form, together with the N to which they are attached, a heterocycloalkyl group.

In certain compounds of Formula IB, $R^1$ is Cl.
In certain compounds of Formula IB, W is O.
In certain compounds of Formula IB, $R^5$ is H or alkyl. In other compounds of Formula IB, $R^5$ is -L-X.
In certain compounds of Formula IB, $R^7$ and $R^8$ are H. In other compounds of Formula IB, $R^7$ and $R^8$ are alkyl.
In certain compounds of Formula IB, each X is $SO_3$H. In other compounds of Formula IB, each X is —$N^+R^aR^bR^c$, wherein $R^a$, $R^b$ and $R^c$ are optionally and independently substituted alkyl or heteroalkyl groups. In certain of these compounds, $R^a$, $R^b$, and $R^c$ is methyl. In other of these compounds, one X can be —$SO_3$H and another X can be —$N^+R^aR^bR^c$ as described above.

In certain compounds of Formula IB, each L is —($CH_2$)—. In other compounds of Formula IB, each L is —($CH_2$—$CH_2$)— or —($CH_2$)$_3$—.

Another aspect of the current disclosure relates to compounds of Formula IC

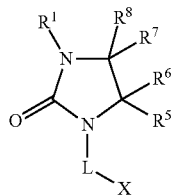

or a salt thereof, wherein:

$R^1$ is Cl or Br, or optionally substituted alkyl or heteroalkyl;

$R^5$ and $R^6$ are each independently H or optionally substituted alkyl or heteroalkyl; or $R^5$ and $R^6$ together with the carbon to which they are attached form a carbonyl or an optionally substituted cycloalkyl or heterocycloalkyl;

$R^7$ and $R^8$ are each independently H or optionally substituted alkyl or heteroalkyl; or $R^7$ and $R^8$ together with the carbon to which they are attached form an optionally substituted cycloalkyl or heterocycloalkyl;

L is independently an optionally substituted $C_{1-6}$ alkyl, heteroalkyl, cycloalkyl or heterocycloalkyl group; and X is independently —$SO_3H$, —$N^+R^aR^bR^c$, —$B(OH)_2$, —$CO_2H$, —$PO_3H_2$ or —$PO_3HR^a$ and $R^a$, $R^b$, and/or $R^c$ are independently and optionally substituted alkyl, heteroalkyl, groups, or may form, together with the N to which they are attached, a heterocycloalkyl group.

In certain compounds of Formula IC, $R^1$ is Cl.

In certain compounds of Formula IC, $R^5$ and $R^6$ are each independently H or optionally substituted alkyl.

In certain compounds of Formula IC, $R^7$ and $R^8$ are each independently H or optionally substituted alkyl.

In certain compounds of Formula IC, X is —$SO_3H$. In other compound of Formula IC, X is —$N^+R^aR^bR^c$, and $R^a$, $R^b$ and $R^c$ are optionally and independently substituted alkyl or heteroalkyl groups.

In certain compounds of Formula IC, L is —$(CH_2)$—. In other compounds of Formula IC, L is —$(CH_2$—$CH_2)$— or —$(CH_2)_3$—.

Another aspect of the current disclosure relates to compounds of Formula ID

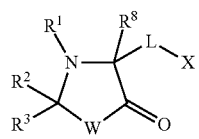

or a salt thereof, wherein:

W is $NR^4$ or O;

$R^1$ is H, Cl, Br or optionally substituted alkyl or heteroalkyl;

$R^2$ and $R^3$ are each independently H or optionally substituted alkyl or heteroalkyl, or $R^2$ and $R^3$ together with the carbon to which they are attached form a carbonyl;

$R^4$ is H, Cl, Br or optionally substituted alkyl or heteroalkyl, with the proviso that $R^1$ and $R^4$ are not both H;

$R^8$ is H, optionally substituted alkyl or heteroalkyl, or -L-X;

each L is independently an optionally substituted $C_{1-6}$ alkyl, heteroalkyl, cycloalkyl or heterocycloalkyl group; and each X is independently —$SO_3H$, —$N^+R^aR^bR^c$, —$B(OH)_2$, —$CO_2H$, —$PO_3H_2$ or —$PO_3HR^a$ and $R^a$, $R^b$, and/or $R^c$ are independently and optionally substituted alkyl, heteroalkyl, groups, or may form, together with the N to which they are attached, a heterocycloalkyl group.

In certain compounds of Formula ID, $R^1$ is Cl.

In certain compounds of Formula ID, W is O.

In certain compounds of Formula ID, $R^2$ and $R^3$ are each independently H or optionally substituted alkyl or heteroalkyl. In certain of these compounds, $R^2$ and $R^3$ are both H. In other of these compounds, $R^2$ and $R^3$ are both alkyl.

In certain compounds of Formula ID, $R^8$ is H or optionally substituted alkyl or heteroalkyl.

In certain compounds of Formula ID, each X is $SO_3H$. In other compounds of Formula ID, each X is —$N^+R^aR^bR^c$, wherein $R^a$, $R^b$ and $R^c$ are optionally and independently substituted alkyl or heteroalkyl groups. In certain of these compounds, $R^a$, $R^b$, and $R^c$ is methyl. In other of these compounds, one X can be —$SO_3H$ and another X can be —$N^+R^aR^bR^c$ as described above.

In certain compounds of Formula ID, each L is —$(CH_2)$—. In other compounds of Formula ID, each L is —$(CH_2$—$CH_2)$— or —$(CH_2)_3$—.

Another aspect of the current disclosure relates to compounds of Formula IE

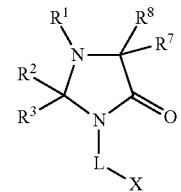

or a salt thereof, wherein:

$R^1$ is Cl, Br or optionally substituted alkyl or heteroalkyl;

$R^2$ and $R^3$ are each independently H or optionally substituted alkyl or heteroalkyl, or $R^2$ and $R^3$ together with the carbon to which they are attached form a carbonyl;

$R^7$ and $R^8$ are each independently H or optionally substituted alkyl or heteroalkyl; or $R^7$ and $R^8$ together with the carbon to which they are attached form an optionally substituted cycloalkyl or heterocycloalkyl group;

L is independently an optionally substituted $C_{1-6}$ alkyl, heteroalkyl, cycloalkyl or heterocycloalkyl group; and X is independently —$SO_3H$, —$N^+R^aR^bR^c$, —$B(OH)_2$, —$CO_2H$, —$PO_3H_2$ or —$PO_3HR^a$ and $R^a$, $R^b$ and/or $R^c$ are independently and optionally substituted alkyl, heteroalkyl, groups, or may form, together with the N to which they are attached, a heterocycloalkyl group.

In certain compounds of Formula IE, $R^1$ is Cl.

In certain compounds of Formula IE, $R^2$ and $R^3$ are each independently H or optionally substituted alkyl or heteroalkyl.

In certain compounds of Formula IE, $R^7$ and $R^8$ are each independently H or optionally substituted alkyl or heteroalkyl.

In certain compounds of Formula IE, X is —$SO_3H$. In other compound of Formula IE, X is —$N^+R^aR^bR^c$, and $R^a$, $R^b$ and $R^c$ are optionally and independently substituted alkyl or heteroalkyl groups.

In certain compounds of Formula IE, L is —$(CH_2)$—. In other compounds of Formula IE, L is —$(CH_2$—$CH_2)$— or —$(CH_2)_3$—.

Another aspect of the current disclosure relates to compounds of Formula IF

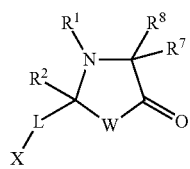

IF or a salt thereof, wherein:

W is $NR^4$ or O;

$R^1$ is H, Cl, Br or optionally substituted alkyl or heteroalkyl;

$R^2$ is H or optionally substituted alkyl, heteroalkyl, or -L-X;

$R^4$ is H, Cl, Br or optionally substituted alkyl or heteroalkyl, with the proviso that $R^1$ and $R^4$ are not both H;

$R^7$ and $R^8$ are each independently H or optionally substituted alkyl or heteroalkyl; or $R^7$ and $R^8$ together with the carbon to which they are attached form an optionally substituted cycloalkyl or heterocycloalkyl;

each L is independently an optionally substituted $C_{1-6}$ alkyl, heteroalkyl, cycloalkyl, or heterocycloalkyl group; and each X is independently —$SO_3H$, —$N^+R^aR^bR^c$, —$B(OH)_2$, —$CO_2H$, —$PO_3H_2$ or —$PO_3HR^a$ and $R^a$, $R^b$, and/or $R^c$ are independently and optionally substituted alkyl, heteroalkyl, groups, or may form, together with the N to which they are attached, a heterocycloalkyl group.

In certain compounds of Formula IF, $R^1$ is Cl.

In certain compounds of Formula IF, $R^2$ is H or optionally substituted alkyl or heteroalkyl.

In certain compounds of Formula IF, $R^7$ and $R^8$ are each independently H or optionally substituted alkyl or heteroalkyl.

In certain compounds of Formula IF, X is —$SO_3H$. In other compound of Formula IE, X is —$N^+R^aR^bR^c$, and $R^a$, $R^b$ and $R^c$ are optionally and independently substituted alkyl or heteroalkyl groups.

In certain compounds of Formula IF, each L is —$(CH_2)$—. In other compounds of Formula IF, each L is —$(CH_2—CH_2)$— or —$(CH_2)_3$—.

Another aspect of the current disclosure relates to compounds of Formula IG

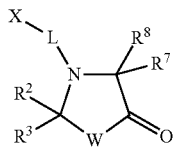

IG or a salt thereof, wherein:

W is $NR^4$ or O;

$R^2$ and $R^3$ are each independently H or optionally substituted alkyl or heteroalkyl, or $R^2$ and $R^3$ together with the carbon to which they are attached form a carbonyl;

$R^4$ is H, Cl, Br or optionally substituted alkyl or heteroalkyl;

$R^7$ and $R^8$ are each independently H or optionally substituted alkyl or heteroalkyl; or $R^7$ and $R^8$ together with the carbon to which they are attached form an optionally substituted cycloalkyl or heterocycloalkyl;

L is independently an optionally substituted $C_{1-6}$ alkyl, heteroalkyl, cycloalkyl or heterocycloalkyl group; and X is independently —$SO_3H$, —$N^+R^aR^bR^c$, —$B(OH)_2$, —$CO_2H$, —$PO_3H_2$ or —$PO_3HR^a$ and $R^a$, $R^b$, and/or $R^c$ are independently and optionally substituted alkyl, heteroalkyl, groups, or may form, together with the N to which they are attached, a heterocycloalkyl group.

In certain compounds of Formula IG, $R^2$ and $R^3$ are each independently H or optionally substituted alkyl or heteroalkyl.

In certain compounds of Formula IG, $R^4$ is Cl.

In certain compounds of Formula IG, $R^7$ and $R^8$ are each independently H or optionally substituted alkyl or heteroalkyl.

In certain compounds of Formula IG, X is —$SO_3H$. In other compound of Formula IF, X is —$N^+R^aR^bR^c$, and $R^a$, $R^b$ and $R^c$ are optionally and independently substituted alkyl or heteroalkyl groups.

In certain compounds of Formula IG, L is —$(CH_2)$—. In other compounds of Formula IG, L is —$(CH_2—CH_2)$— or —$(CH_2)_3$—.

The present application also includes the compounds in Table 1, hereby identified by name, structure, and reference number. These and other compounds may be named or depicted with or without a particular counter ion (e.g., chloride or Cl⁻). It will nevertheless be understood that in those cases, the associated cation and any other salt form (e.g., the corresponding bromide, carbonate, hydroxide, etc.), as well as the particular salt named or depicted, may also be contemplated and are within the scope of this disclosure.

TABLE 1

| Name (Compound No.) | Structure |
|---|---|
| (3-chloro-4-methyl-2-oxooxazolidin-4-yl)methanesulfonic acid (22-01) | 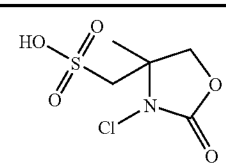 |
| (3-bromo-4-methyl-2-oxooxazolidin-4-yl)methanesulfonic acid (22-02) | 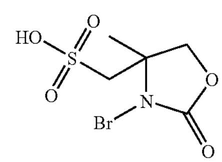 |
| (3-chloro-4-methyl-2-oxooxazolidin-4-yl)methanephosphonic acid (22-03) | 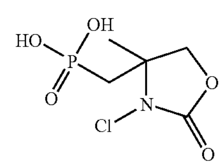 |
| 1-(3-chloro-4-methyl-2-oxooxazolidin-4-yl)-N,N,N-trimethylmethanaminium chloride (22-04) | 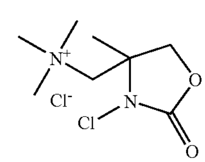 |
| (3-chloro-4-ethyl-2-oxooxazolidin-4-yl)methanesulfonic acid (22-05) | 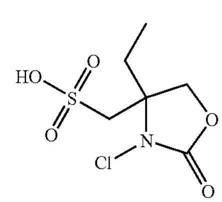 |

TABLE 1-continued

| Name (Compound No.) | Structure |
|---|---|
| (4R,5S)-(3-chloro-4,5-dimethyl-2-oxooxazolidin-4-yl)methanesulfonic acid (22-06) | 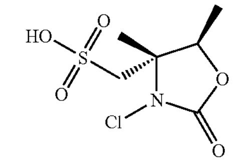 |
| (4R,5R)-(3-chloro-4,5-dimethyl-2-oxooxazolidin-4-yl)methanesulfonic acid (22-07) | 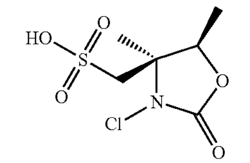 |
| (3-chloro-4,5,5-trimethyl-2-oxooxazolidin-4-yl)methanesulfonic acid (22-08) | 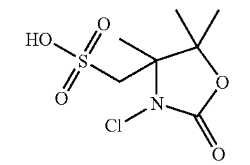 |
| 2-(3-chloro-4-methyl-2-oxooxazolidin-4-yl)ethanesulfonic acid (22-09) | 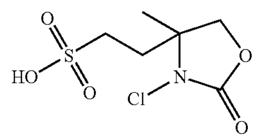 |
| (3-chloro-4-methyl-2-oxoimidazolidin-4-yl)methanesulfonic acid (22-10) | 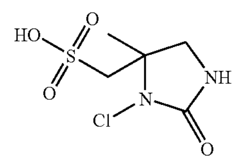 |
| (1-chloro-4,5,5-trimethyl-2-oxoimidazolidin-4-yl)methanesulfonic acid (22-11) | 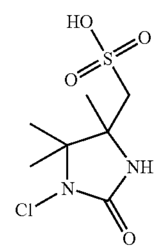 |
| (3-chloro-2-oxooxazolidine-4,4-diyl)dimethanesulfonic acid (22-12) | 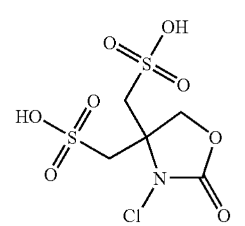 [SMILES: O=C1OCC(CS(=O)(=O)O)(CS(=O)(=O)O)N1Cl] |
| (3-chloro-2-oxo-4-((trimethylammonio)methyl)oxazolidin-4-yl)methanesulfonic acid (22-13) | 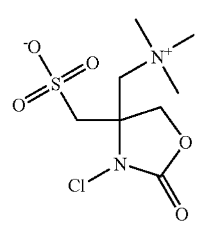 |
| (3-dichloro-4-methyl-2-oxoimidazolidin-4-yl)methanesulfonic acid (22-14) | 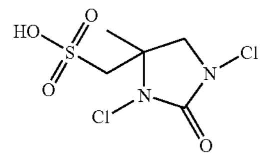 |
| (3-bromo-1-chloro-4-methyl-2-oxoimidazolidin-4-yl)methanesulfonic acid (22-15) | 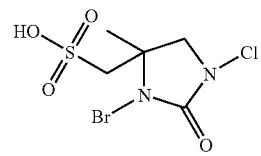 |
| (1-bromo-3-chloro-4-methyl-2-oxoimidazolidin-4-yl)methanesulfonic acid (22-16) | 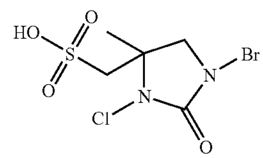 |
| (3-dichloro-4-methyl-2-oxo-1,3-diazaspiro[4.4]nonan-4-yl)methanesulfonic acid (22-17) | 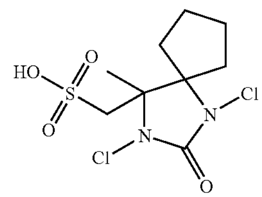 [SMILES: CC1(CS(=O)(=O)O)N(Cl)C(=O)N(Cl)C12CCCC2] |
| (3-chloro-5-methyl-2-oxooxazolidin-5-yl)methanesulfonic acid (22-18) | 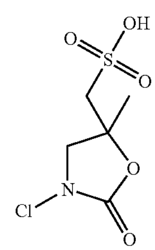 |
| (3-chloro-4,4,5-trimethyl-2-oxooxazolidin-5-yl)methanesulfonic acid (22-19) | 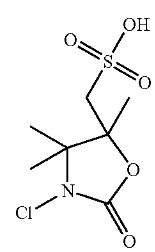 |
| (1-chloro-4-methyl-2-oxoimidazolidin-4-yl)methanesulfonic acid (22-20) | 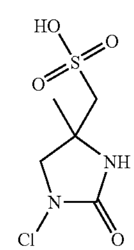 |

TABLE 1-continued

| Name (Compound No.) | Structure |
| --- | --- |
| (3-chloro-1,4-dimethyl-2,5-dioxoimidazolidin-4-yl)methanesulfonic acid (22-21) | 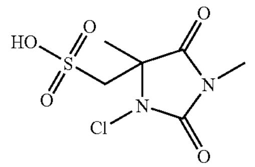 |
| (3-dichloro-4-methyl-2,5-dioxoimidazolidin-4-yl)methanesulfonic acid (22-22) | 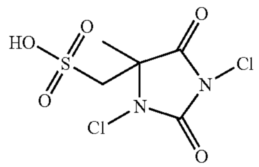 |
| 2-(3-chloro-4,4,5,5-tetramethyl-2-oxoimidazolidin-1-yl)ethanesulfonic acid (22-23) | 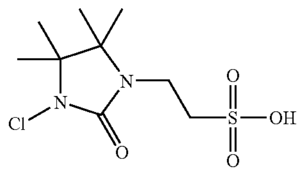 [SMILES: CC1(C)N(Cl)C(=O)N(CCS(=O)(=O)O)C1(C)C] |
| 2-(3-chloro-4,4-dimethyl-2,5-dioxoimidazolidin-1-yl)ethanesulfonic acid (22-24) | 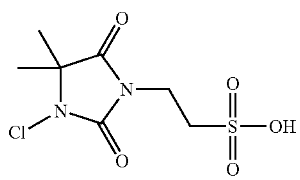 [SMILES: CC1(C)C(=O)N(CCS(=O)(=O)O)C(=O)N1Cl] |
| 2-(1,8-dichloro-7,7,9,9-tetramethyl-2,4-dioxo-1,3,8-triazaspiro[4.5]decan-3-yl)ethanesulfonic acid (22-25) | 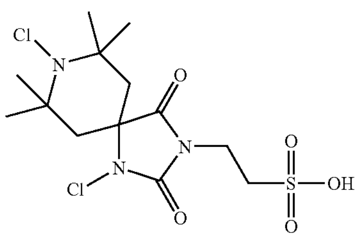 [SMILES: CC1(C)CC2(CC(C)(C)N1Cl)C(=O)N(CCS(=O)(=O)O)C(=O)N2Cl] |
| 2-(3-chloro-5,5-dimethyl-2,4-dioxoimidazolidin-1-yl)ethanesulfonic acid (22-26) | 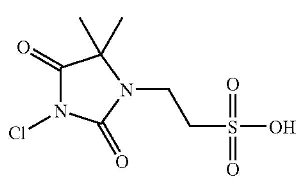 [SMILES: CC1(C)C(=O)N(Cl)C(=O)N1CCS(=O)(=O)O] |
| 1-(3-chloro-1,4-dimethyl-2,5-dioxoimidazolidin-4-yl)-N,N,N-trimethylmethanaminium chloride (22-27) | 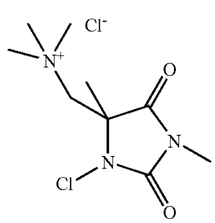 |
| 2-(3-chloro-1,2,2,4-tetramethyl-5-oxoimidazolidin-4-yl)ethanesulfonic acid (22-28) | 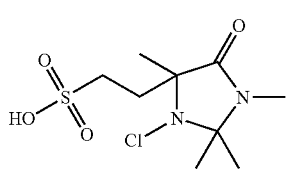 [SMILES: CN1C(=O)C(C)(CCS(=O)(=O)O)N(Cl)C1(C)C] |
| 2-(1,3-dichloro-2,2,4-trimethyl-5-oxoimidazolidin-4-yl)ethanesulfonic acid (22-29) | |
| 2-(1-chloro-1,2,2,4-tetramethyl-5-oxoimidazolidin-4-yl)ethanesulfonic acid (22-30) | |
| 2-(3-chloro-2,2,4,4-tetramethyl-5-oxoimidazolidin-1-yl)ethanesulfonic acid (22-31) | |
| 2-(3-chloro-1,2,4,4-tetramethyl-5-oxoimidazolidin-2-yl)ethanesulfonic acid (22-32) | |
| 2-(1,3-dichloro-2,4,4-trimethyl-5-oxoimidazolidin-2-yl)ethanesulfonic acid (22-33) | |
| 2-(3-chloro-2,2,5,5-tetramethyl-4-oxoimidazolidin-1-yl)ethanesulfonic acid (22-34) | |
| 1-(3-chloro-2-oxooxazolidin-5-yl)-N,N,N-trimethylmethanaminium chloride (22-35) | |

TABLE 1-continued

| Name (Compound No.) | Structure |
|---|---|
| 3-chloro-8,8-dimethyl-2-oxo-1-oxa-3-aza-8-azoniaspiro[4.5]decane chloride (22-36) | |
| 1,3-dichloro-8,8-dimethyl-2,4-dioxo-1,3-diaza-8-azoniaspiro[4.5]decane (22-37) | |
| N-((3-chloro-4-methyl-2-oxooxazolidin-4-yl)methyl)-N, N-dimethylethanaminium chloride (22-38) | |
| 2-((3-Chloro-4-methyl-2-oxooxazolidin-4-yl)methylsulfonyl)ethanesulfonic acid (22-39) | |
| 1-((3-chloro-4-methyl-2-oxooxazolidin-4-yl)methyl)-1-methylpyrrolidinium chloride (22-40) | |
| 3-(3-chloro-2,2,4,4-tetramethyl-5-oxoimidazolidin-1-yl)-N,N,N-trimethylpropan-1-aminium chloride (22-41) | |
| 3-(3-chloro-2,2,5,5-tetramethyl-4-oxoimidazolidin-1-yl) N,N,N-trimethylpropan-1-aminium chloride (22-42) | 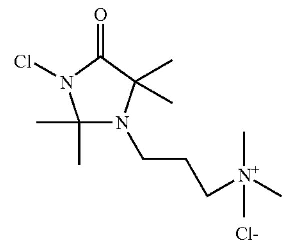 [SMILES: CC1(C)C(=O)N(Cl)C(C)(C)N1CCC[N+](C)(C)C ; [Cl-]] |
| 3-(3-chloro-2,2,4,4-tetramethyl-5-oxoimidazolidin-1-yl)propane-1-sulfonic acid (22-43) | 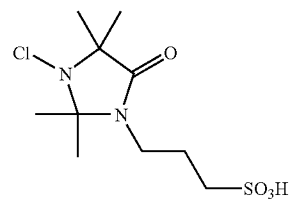 [SMILES: CC1(C)C(=O)N(CCCS(=O)(=O)O)C(C)(C)N1Cl] |
| 3-(3-chloro-2,2,5,5-tetramethyl-4-oxoimidazolidin-1-yl)propane-1-sulfonic acid (22-44) | 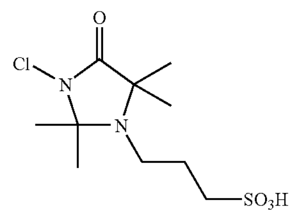 [SMILES: CC1(C)C(=O)N(Cl)C(C)(C)N1CCCS(=O)(=O)O] |
| 2-(3-chloro-4,4-dimethyl-2-oxooxazolidin-5-yl)-N,N,N-trimethylethanaminium chloride (22-45) | 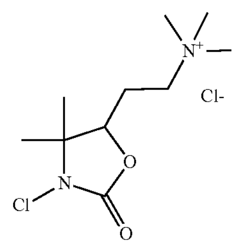 |
| 2-(3-chloro-4,4-dimethyl-2-oxooxazolidin-5-yl)ethanesulfonic acid (22-46) | 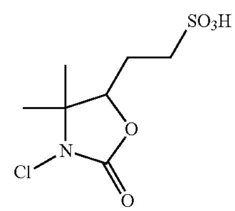 |
| 2-(3-chloro-4,4-dimethyl-2-oxooxazolidin-5-yl)-N,N,N-trimethylethanaminium chloride (22-47) | 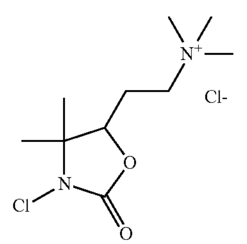 |
| 2-(3-chloro-5,5-dimethyl-2,4-dioxoimidazolidin-1-yl)-N,N,N-trimethylethanaminium chloride (22-48) | 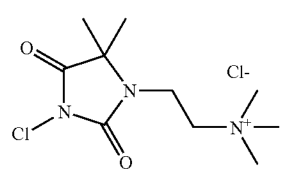 [SMILES: CC1(C)C(=O)N(Cl)C(=O)N1CC[N+](C)(C)C ; [Cl-]] |

TABLE 1-continued

| Name (Compound No.) | Structure |
| --- | --- |
| 2-(3-Chloro-4,4-dimethyl-2-oxoimidazolidin-1-yl)-N,N,N-trimethylethanaminium acetate (22-49) | 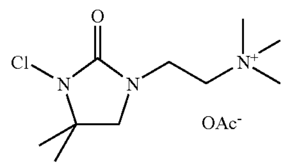 |
| 1-chloro-8,8-dimethyl-2-(N,N-dimethyl-piperdin-4-ium)-4-oxo-1,3-diaza-8-azoniaspiro[4.5]decane dichloride (22-50) | 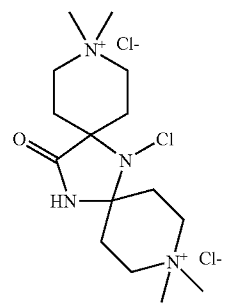 [SMILES: C[N+]1(C)CCC2(CC1)NC(=O)C1(CC[N+](C)(C)CC1)N2Cl ; [Cl-] ; [Cl-]] |

The starting materials and reagents employed in preparing these compounds and analogs or derivatives are either available from commercial suppliers such as Sigma-Aldrich Chemical Company (Milwaukee, Wis., USA), TCI America (Portland, Oreg., USA), Matrix Scientific (Columbia, S.C., USA), VWR International (Pasadena, Calif., USA), Fisher Scientific (Chicago, Ill., USA), Alfa Aesar (Wood Hill, Mass., USA), Advanced Chem Tech (Louisville, Ky., USA), Chem Impex (Chicago, Ill., USA), and Advanced Asymmetries (Belleville, Ill., USA) or are prepared by methods known in the art following procedures available in references such as *Protective Groups in Organic Synthesis* (John Wiley & Sons, 3$^{rd}$ Edition), *Protective Groups, Foundation of Organic Chemistry* (Thieme & Sons Inc.), *Fieser and Fieser's Reagents for Organic Synthesis*, Volumes 1-15 (John Wiley and Sons, 1991), *Rodd's Chemistry of Carbon Compounds*, Volumes 1-15 and Supplemental Materials (Elsevier Science Publishers, 1989), *Organic Reactions*, Volume 1-40 (John Wiley & Sons, 1991), *March's Advanced Organic Chemistry* (John Wiley & Sons, 4$^{th}$ Edition), and *Larock's Comprehensive Organic Transformation* (VCH Publishers Inc., 1989).

Various chlorine sources may be used to produce the N-chlorinated compounds, e.g., chlorine itself (i.e., $Cl_2$ gas), certain N-chloroarylsulfonamide salts, wherein the aryl group contains from about 6 to about 15 carbon atoms with 1 or 2 aromatic rings, 6 to 10 or 6 to 8 carbon atoms and one aromatic ring, such as N-chlorobenzene-sulfonamide or N-chloro-4-alkylbenzenesulfonamide, wherein the alkyl group is an alkyl from about 1 to about 4 carbons, such as methyl or ethyl. The N-chlorobenzene-sulfonamides or N-chloro-4-alkylbenzenesulfonamides are often used in the form of their salts, e.g., alkali salts, e.g., sodium or potassium salts. Frequently used reagents include N-chlorobenzene-sulfonamide and N-chloro-4-methyl-benzenesulfonamide in the form of their sodium salts, because they are readily commercially available. Other non-limiting chlorinating agents include HOCl and N-chlorosuccinimide.

Compounds of Formula I (which include compounds of Formulae IA, IB, IC, ID, IE, IF and IG) may be prepared according to the following schemes, in addition to other standard manipulations known in the art. These schemes are illustrative and are not limiting. Compound numbers shown in the schemes do not necessarily correlate to compound numbers used in Table 1 or the Examples.

Scheme 1

Certain compounds of Formula I wherein W is O, and $R^6$ is -L-X wherein X is $—N^+R^aR^bR^c$, may be prepared according to the following exemplary generalized scheme.

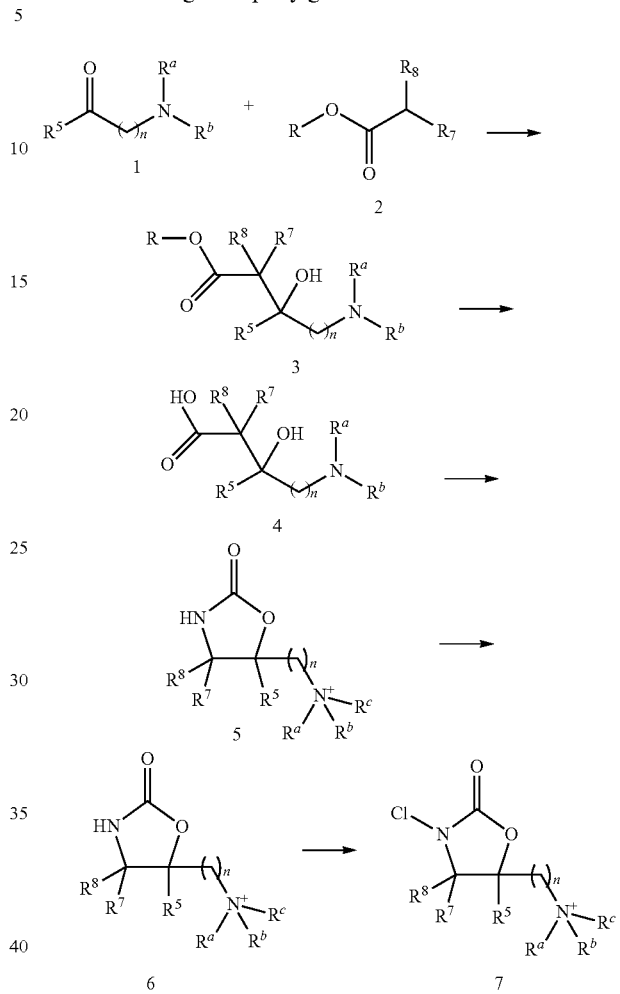

Step 1-1: Compound 2 can be activated with the use of a suitable base, such as lithium hexamethyldisilylamide (also referred to as hexamethyldisilazide) or lithium diisoproylamine in an aprotic solvent, such as tetrahydrofuran. After stirring for about 10 to about 60 minutes at −78° C. to −30° C., the reaction mixture is treated with compound 1. The combined reaction mixture is generally conducted at −78° C. to room temperature for a period of about 30 minutes to about 8 hours.

Step 1-2: Hydrolysis of compound 3 under typical saponification conditions can provide compound 4. Standard saponification procedures generally use a polar solvent such as water, methanol or ethanol. Appropriate bases include sodium hydroxide or lithium hydroxide. The reaction is usually conducted at room temperature to reflux for a period of about 1 to about 24 hours.

Step 1-3: Compound 5 can be obtained by treating compound 4 with diphenylphosphorlylazide in a non-polar solvent, such as toluene or xylenes. The reaction is generally conducted for a period of about 1 to about 24 hours.

Step 1-4: The quarternization of the amine in compound 5 can be carried out with an alkylating agent in the presence or absence of a base to provide the product 6. Suitable alkylating agents include alkyl halides such as methyl iodide, and the like. The alkylation may be conducted neat with excess of alkylating reagent or in an inert organic solvent such as, for example, N,N-dimethylformamide, acetonitrile, dichloromethane, alcohols or N-methylpyridone. Suitable bases include N,N-diisopropyl ethylamine, triethylamine, cesium carbonate and the like. The reaction is typically conducted at room temperature to 100° C. for about 16 to about 48 hours.

Step 1-5: N-Chlorination of compound 6 can be accomplished by treatment with a chlorinating agent such as tert-butyl hypochlorite, trichloroisocyanuric acid, sodium hypochlorite, N-chlorosuccinimide, N-chlorohydantoins and chlorine gas in a polar solvent such as water, N,N-dimethylformamide, methylene chloride, and the like, to give compound 7. The reaction is typically carried out at low temperature to ambient temperature for about 2 to about 24 hours.
Scheme 2

Certain compounds of Formula I, wherein $R^5$ and $R^6$ form a heterocyloalkyl, may be prepared according to the following exemplary generalized scheme wherein a and b are integers from 1 to 4 and PG is a suitable protecting group.

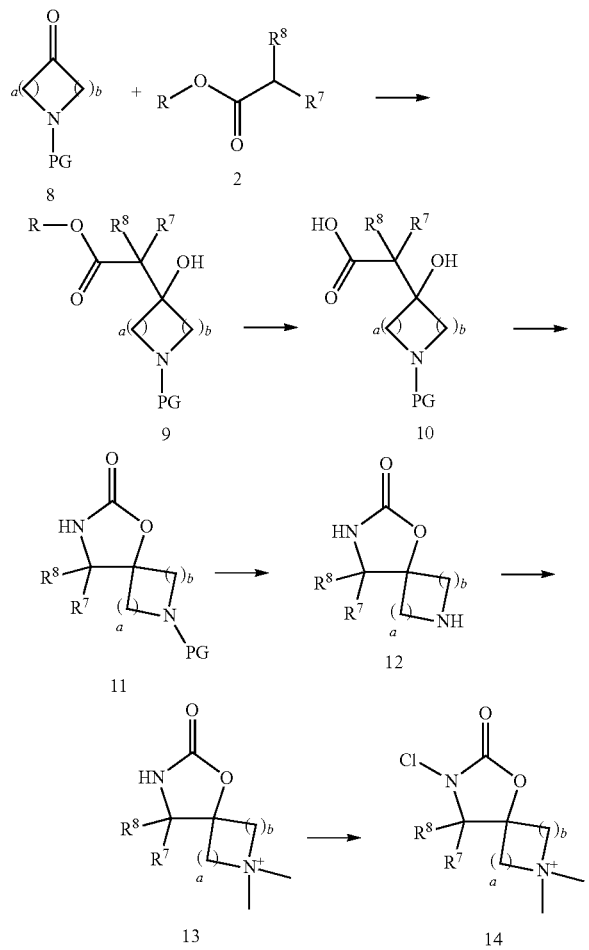

Step 2-1: Compound 2 can be activated with the use of a suitable base, such as lithium hexamethyldisilylamide or lithium diisopropylamine in an aprotic solvent, such as tetrahydrofuran. After stirring for about 10 to about 60 minutes at −78° C. to −30° C., the reaction mixture is treated with compound 8. The combined reaction mixture is generally conducted at −78° C. to room temperature for a period of about 30 minutes to about 8 hours.

Step 2-2: Hydrolysis of compound 9 under typical saponification conditions can provide compound 10. The standard procedures generally use a polar solvent such as water, methanol or ethanol, and appropriate bases include sodium hydroxide and lithium hydroxide. The reaction is usually conducted at room temperature to reflux for a period of about 1 to about 24 hours.

Step 2-3: Compound 11 can be obtained by treating compound 10 with diphenylphosphorlyazide in a non-polar solvent, such as toluene or xylenes. The reaction is generally conducted for a period of about 1 to about 24 hours.

Step 2-4: N-Deprotection of compound 11 may be carried out using methods well known to those of skill in the art and would depend on the protecting group used (see, e.g., Greene, supra). For example, in the case of N-Boc, HCl in dioxane or TFA in DCM can be used. An example for the case with Cbz, HBr in acetic acid may be used. Cbz may also be removed by a metal-catalyzed hydrogenation, such as with palladium on carbon, in a polar solvent, such as methanol or ethanol. The reactions are generally performed at 0° C. to room temperature for about 16 to about 48 hours. The hydrogenation reaction is generally performed under 1 to 30 atmospheres of hydrogen.

Step 2-5: The quaternization of the amine of compound 12 can be carried out with an alkylating agent with or without basic catalysis to provide the product 13. Suitable alkylating agents include alkyl halides such as methyl iodide and the like. The alkylation may be conducted neat with excess of alkylating reagent or in an inert organic solvent such as, for example, N,N-dimethylformamide, acetonitrile, dichloromethane, alcohols or N-methylpyridone. Suitable bases include N,N-diisopropyl ethylamine, triethylamine, cesium carbonate and the like. The reaction is typically conducted at room temperature to about 100° C. for about 16 to about 48 hours.

Step 2-6: N-Chlorination of compound 13 can be accomplished by treatment with a chlorinating agent such as tert-butyl hypochlorite, trichloroisocyanuric acid, sodium hypochlorite, N-chlorosuccinimide, N-chlorohydantoins and chlorine gas in a polar solvent such as water, N,N-dimethylformamide, methylene chloride and the like to give compound 14. The reaction is typically carried out at low temperature to ambient temperature for about 2 to about 24 hours.
Scheme 3

Certain compounds of Formula I, wherein W is $NR^4$ wherein $R^4$ is -L-X, may be prepared according to the following exemplary generalized scheme.

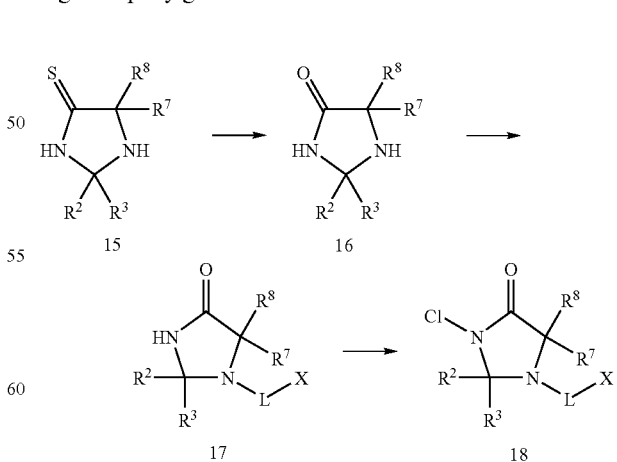

Step 3-1: The thione 15 (see, e.g., U.S. Pat. No. 5,057,612) can be oxidized to compound 16 with an oxidizing agent. A suitable oxidizing agent may include hydrogen peroxide and the like, in polar solvent, such as water, alcohol, and the like. The reaction is typically conducted at 0° C. to about 60° C. for about 30 minutes to about 24 hours.

Step 3-2: The alkylation reaction, to attach the linker (L) and water solubilizing groups (X) on to the amine of compound 16, can be carried out with linker and water solubilizing groups which possess a displaceable halide. This may be accomplished with or without a mildly basic catalysis to provide the product 17. A suitable alkylating reagent may include 3-bromopropanesulfonic acid sodium salt and the like, or (3-bromopropyl)trimethylammonium bromide and the like, or 4-iodobutyric acid and the like. The alkylation may be conducted in an inert organic solvent such as, for example, N,N-dimethylformamide, acetonitrile, dichloromethane or N-methylpyridone. Suitable bases include N,N-diisopropyl ethylamine, cesium carbonate and the like. The reaction is typically conducted at room temperature to about 100° C. for about 16 to about 48 hours.

Step 3-3: N-Chlorination of compound 17 can be accomplished by treatment with a chlorinating agent such as tert-butyl hypochlorite, trichloroisocyanuric acid, sodium hypochlorite, N-chlorosuccinimide, N-chlorohydantoins and chlorine gas in a polar solvent such as water, N,N-dimethylformamide, methylene chloride and the like to give compound 18. The reaction is typically carried out at low temperature to ambient temperature for about 2 to about 24 hours.

Scheme 4

Certain compounds of Formula I, wherein W is $NR^4$ and $R^4$ is Cl, may be prepared according to the following exemplary generalized scheme.

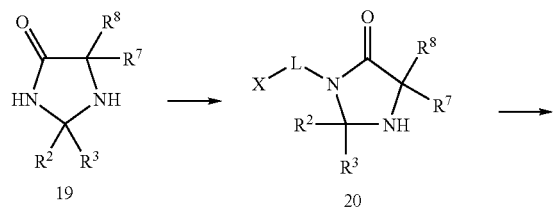

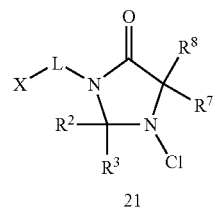

Step 4-1: The alkylation reaction, to attach the linker (L) and water solubilizing groups (X) on to the amide of compound 19 to provide the product 20, can be carried out with a strong base. A suitable base may include sodium hydride, lithium bis(trimethylsilyl)amide, butyllithium and the like. After treatment with a base, the reaction is treated with an alkylating agent. A suitable alkylating reagent may include 3-bromopropanesulfonic acid sodium salt and the like, or (3-bromopropyl)trimethylammonium bromide and the like, or 4-iodobutyric acid sodium salt and the like. The alkylation may be conducted in an inert organic solvent such as, for example, N,N-dimethylformamide, acetonitrile, tetrahydrofuran, dichloromethane, or N-methylpyridone. The reaction is typically conducted at −78° C. to about 90° C. for about 16 to about 48 hours.

Step 4-2: N-Chlorination of compound 20 can be accomplished by treatment with a chlorinating agent such as tert-butyl hypochlorite, trichloroisocyanuric acid, sodium hypochlorite, N-chlorosuccinimide, N-chlorohydantoins and chlorine gas in a polar solvent such as water, N,N-dimethylformamide, methylene chloride and the like to give compound 21. The reaction is typically carried out at low temperature to ambient temperature for about 2 to about 24 hours.

Scheme 5

Certain compounds of Formula I, wherein W is $NR^4$, and $R^4$ is an -L-X wherein X is —$SO_3H$ or —$N^+R^aR^bR^c$, may be prepared according to the following exemplary generalized scheme.

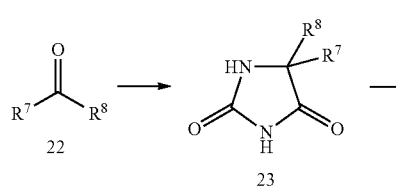

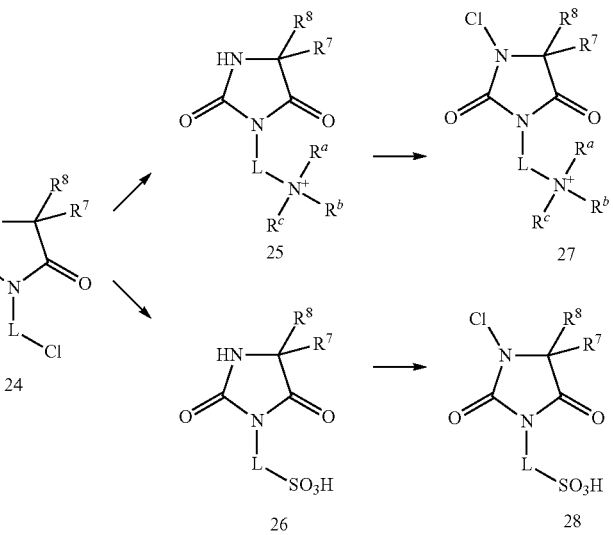

Step 5-1: Ketone 22 may be converted to the hydantoin 23 by treatment with ammonium carbonate and potassium cyanide in a polar solvent such as methanol, water, and the like. The reaction is typically carried out at ambient temperature to 90° C. for about 6 hours to about 3 days.

Step 5-2: The hydantoin 23 may be alkylated with a dihalogenated alkane such as 1-bromo-2-chloroethane, 1-bromo-3-chloropropaneane, and the like to give compound 24. The reaction is typically conducted with a base, such as potassium hydroxide and the like, at 50° C. to 90° C. for about 6 hours to about 3 days in a polar solvent such as ethanol, water, and the like.

Step 5-3a: Compound 24 may be converted to ammonium compound 25 by displacement of the chloride with amine such as dimethylamine and the like, or piperidine and the like in the presence of a base. This is followed by treatment with an alkyl halide such as methyl iodide and the like. The reaction is typically conducted in an inert organic solvent such as, for example, N,N-dimethylformamide, acetonitrile, dichloromethane, alcohols or N-methylpyridone at room temperature to about 100° C. for about 16 to about 48 hours. Suitable bases include N,N-diisopropyl ethylamine, triethylamine, cesium carbonate and the like.

Step 5-4a: N-Chlorination of compound 25 can be accomplished by treatment with a chlorinating agent such as tert-butyl hypochlorite, trichloroisocyanuric acid, sodium hypochlorite, N-chlorosuccinimide, N-chlorohydantoins and chlorine gas in a polar solvent such as water, N,N-dimethylformamide, methylene chloride and the like to give compound 27. The reaction is typically carried out at low temperature to ambient temperature for about 2 to about 24 hours.

Step 5-3b: Compound 24 may be converted to the sulfonic acid 26 with potassium thioacetate with an inert solvent such as N,N-dimethylformamide and the like at 50° C. to 100° C. for 1 to 6 hours, followed by oxidation with hydrogen peroxide in formic acid at room temperature for 1 to 24 hours.

Step 5-4b: N-Chlorination of compound 26 can be accomplished by treatment with a chlorinating agent such as tert-butyl hypochlorite, trichloroisocyanuric acid, sodium hypochlorite, N-chlorosuccinimide, N-chlorohydantoins and chlorine gas in a polar solvent such as water, N,N-dimethylformamide, methylene chloride and the like to give compound 28. The reaction is typically carried out at low temperature to ambient temperature for about 2 to about 24 hours.

Scheme 6

Certain compounds of Formula I, wherein W is O, and $R^7$ is -L-X wherein X is $-SO_3H$ or $-N^+R^aR^bR^c$, may be prepared according to the following exemplary generalized scheme.

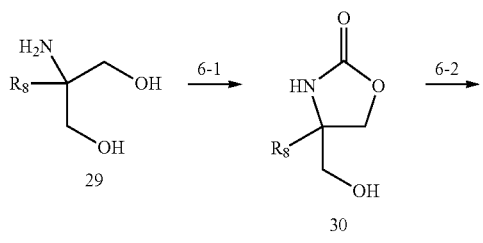
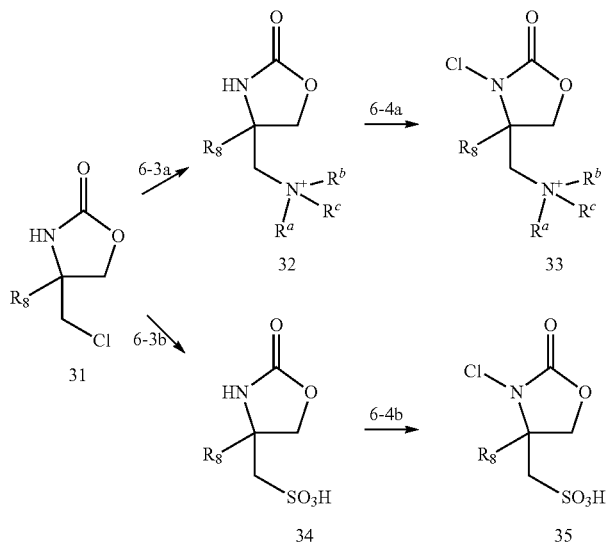

Step 6-1. A 2-amino-1,3-diol (29) can be cyclized to the oxazolidin-2-one (30) by heating with neat diethyl carbonate at 130° C. to 150° C. for several hours, using a Dean-Stark trap to collect the ethanol generated by the reaction.

Step 6-2. The resulting 4-hydroxymethyl-oxazolidin-2-one (30) can be reacted with a dehydrating reagent such as thionyl chloride or phosphorous pentachloride in an aprotic solvent such as dichloromethane or pyridine. Typically the reaction is conducted at 0° C. or room temperature and the reaction is done in two to eight hours.

Step 6-3a. Compound 31 can be converted to the trialkylammonium salt by treatment with a secondary amine such as dimethylamine or pyrrolidine at elevated temperatures (typically 60-90° C.) in an aprotic solvent such as tetrahydrofuran in a sealed tube for 8-24 hours. Subsequent treatment with an alkylating agent such as methyl iodide or ethyl triflate gives Compound 32. The alkylation is typically performed in a protic solvent such as methanol or ethanol at room temperature for 3-24 hours.

Step 6-4a. N-Chlorination of compound 32 can be accomplished by treatment with a chlorinating agent such as tert-butyl hypochlorite, trichloroisocyanuric acid, sodium hypochlorite, N-chlorosuccinimide, N-chlorohydantoins and chlorine gas in a polar solvent such as water, N,N-dimethylformamide, methylene chloride and the like to give compound 33. The reaction is typically carried out at low temperature to ambient temperature for about 2 to about 24 hours.

Step 6-3b. Compound 31 can be reacted with sodium sulfite in a water-dimethylformamide mixture to give the sulfonate, Compound 33. Typically the reaction requires heating to 40-60° C. and takes 3-8 hours.

Step 6-4b. N-Chlorination of compound 33 can be accomplished by treatment with a chlorinating agent such as tert-butyl hypochlorite, trichloroisocyanuric acid, sodium hypochlorite, N-chlorosuccinimide, N-chlorohydantoins and chlorine gas in a polar solvent such as water, N,N-dimethylformamide, methylene chloride and the like to give compound 34. The reaction is typically carried out at low temperature to ambient temperature for about 2 to about 24 hours.

Scheme 7

Certain compounds of Formula I, wherein W is $NR^4$, and $R^4$ is-L-X wherein X is $N^+R^aR^bR^c$, may be prepared according to the following exemplary generalized scheme.

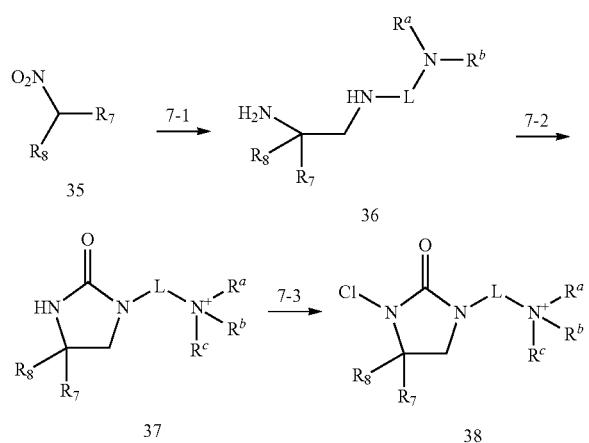

Step 7-1. A nitroalkane (35) such as 2-nitropropanol or nitrocyclohexane can be reacted with formaldehyde, an amine (such as $N^1,N^1$-dimethyl-1,2-diaminoethane) and a catalytic amount of a base such as sodium hydroxide in isopropanol. The reaction is typically complete after 3-24 hours. The resulting product is stirred vigorously with a hydrogenation catalyst such as palladium or Raney(R) Nickel under a pressurized hydrogen atmosphere (400-500 psi) at room temperature in a protic solvent such as methanol or ethanol. The reaction typically takes 10-24 hours.

Step 7-2. The diamine is cyclized using carbonyl diimidazole (CDI) in a solvent such as dichloromethane or dimethylformamide. The reaction typically takes 1-3 hours, and the resulting material can be alkylated with an alkylating reagent such as methyl iodide or ethyl triflate in order to form the quaternary ammonium salt (37). The alkylation is typically performed in a protic solvent such as methanol or ethanol at room temperature for 3-24 hours.

Step 7-3. N-Chlorination of compound 37 can be accomplished by treatment with a chlorinating agent such as tert-butyl hypochlorite, trichloroisocyanuric acid, sodium hypochlorite, N-chlorosuccinimide, N-chlorohydantoins and chlorine gas in a polar solvent such as water, N,N-dimethylformamide, methylene chloride and the like to give compound 38. The reaction is typically carried out at low temperature to ambient temperature for about 2 to about 24 hours.

Scheme 8

Certain compounds of Formula I, wherein W is $NR^4$, and $R^7$ is -L-X wherein X is $—SO_3H$, may be prepared according to the following exemplary generalized scheme.

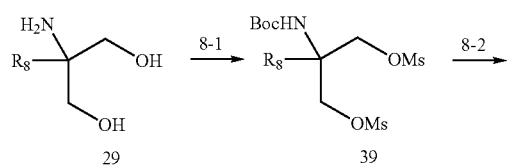

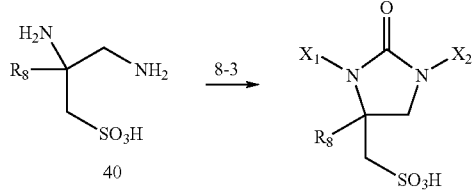

Step 8-1. A 2-amino-1,3-diol (29) such as 2-amino-2-methyl-1,3-propanediol can be reacted with an N-protected reagent such as Boc anhydride in a solvent such as dichloromethane or dimethylformamide. The reaction is typically run between 0° C. and room temperature for 1-18 hours. The resulting material can be reacted with a mesylating agent such as mesyl chloride or mesyl anhydride in the presence of a base such as triethylamine or pyridine in a solvent such as dichloromethane or tetrahydrofuran to give Compound 39. The reaction is typically run at 0° C. for 1-3 hours.

Step 8-2. Removal of the Boc protecting group can be accomplished using a strong acid such as hydrogen chloride or trifluoroacetic acid in a solvent such as 1,4-dioxane or dichloromethane. The reaction is typically run at 0° C. or RT for 30 min to 6 h. The residue is then treated with one equivalent of sodium azide in water for 0.5-1 h, and then one equivalent of sodium sulfite in water for 0.5-1 h. The resulting material is hydrogenated in a solvent such as methanol or ethanol using hydrogen pressures of 1-5 atmospheres for 1-24 hours to give compound 40.

Step 8-3. The diamine 40 is cyclized using carbonyl diimidazole (CDI) in a solvent such as dichloromethane or dimethylformamide. The reaction typically takes 1-3 hours. N-Chlorination of the cyclized compound can be accomplished by treatment with a chlorinating agent such as tert-butyl hypochlorite, trichloroisocyanuric acid, sodium hypochlorite, N-chloro succinimide, N-chlorohydantoins and chlorine gas in a polar solvent such as water, N,N-dimethylformamide, methylene chloride and the like to give compound 41. The reaction is typically carried out at low temperature to ambient temperature for about 2 to about 24 hours.

More specific synthetic routes to illustrative compounds of Formula I are given in the Examples below.

Salts of the compounds of the present application may be prepared by reacting the free acid or base moieties of these compounds, where present, with a stoichiometric or greater amount of the appropriate base or acid in water or in an organic solvent, or in a mixture of the two; generally, e.g., non-aqueous media like ether, ethyl acetate, ethanol, isopropanol. The salts of the present application may also be prepared by ion exchange.

Compounds of Formula I may be formulated as solids, liquids, gels, aerosols, and other forms. For example, solid formulations may consist primarily of a compound of Formula I as a salt. Compositions comprising one or more compounds of Formula I and one or more other substances (e.g. excipients) may be formed, and may take the form of aerosols, creams, emulsions, gels, lotions, ointments, pastes, powders, solutions, suspensions, and other forms suitable for their intended use or application.

Compositions may also include multiple (e.g. two or more) compounds of Formula I. The compositions may also comprise other active ingredients, such as HOCl, OM and other antimicrobial agents.

Compositions or formulations may include a pharmaceutically acceptable carrier, as defined above. By way of example, the compositions of the present application may include the following pharmaceutically acceptable carriers: sodium chloride to attain isotonicity, buffers, stabilizers, solvents, flavoring agents (in case of oral or nasopharyngeal administration or the food industry), preserving agents, diluents, extenders and other auxiliary substances or excipients. Examples of pharmaceutically acceptable carriers and excipients that may be used are described in *Remington: The Science and Practice of Pharmacy*, R. Hendrickson, ed., 21st edition, Lippincott, Williams & Wilkins, Philadelphia, Pa., (2005) at pages 317-318, which are hereby incorporated by reference in their entireties. In general, water, saline, oils, alcohols (e.g. 2-propanol, 1-butanol, etc.), polyols (e.g. 1,2-propanediol, 2,3-butanediol, etc.), and glycols (e.g. propylene glycol, polyethylene glycols, etc.) may be suitable carriers for solutions. In one aspect solutions contain the active ingredient in a water soluble or aqueous medium soluble form, e.g. as a salt, together with suitable stabilizing agents, and if necessary, buffer substances.

For example, compounds of Formula I may be formulated with cyclodextrin or cyclodextrin derivatives, including cyclodextrin sulfobutyl ether (Capisol®, Cydex, Overland Park, Kans., USA). These and other carriers may be used to improve or otherwise modulate the solubility, penetration, uptake, and other properties of compositions comprising the compounds described herein.

Aerosols can range from colloidal dispersions to formulations designed for pressurized delivery. Modes of operation include liquefied-gas systems, compressed-gas systems, and barrier-type systems.

Creams are viscous liquids or semisolid emulsions, either oil-in-water or water-in-oil. Cream bases are water-washable, and contain an oil phase, an emulsifier and an aqueous phase. The oil phase, also called the "internal" phase, is generally comprised of petrolatum and a fatty alcohol such as cetyl or stearyl alcohol. The aqueous phase usually, although not necessarily, exceeds the oil phase in volume, and generally contains a humectant. The emulsifier in a cream formulation is generally a nonionic, anionic, cationic or amphoteric surfactant.

Emulsions are two-phase systems prepared by combining two immiscible liquids, in which small globules of one liquid are dispersed uniformly throughout the other liquid. Emulsions may be designated as oil-in-water or water-in-oil type emulsions. Certain emulsions may not be classified as such because they are described by another category, such as a lotion, cream, and the like.

Gels are semisolid, suspension-type systems. Single-phase gels contain organic macromolecules distributed substantially uniformly throughout the carrier liquid, which is typically aqueous, but also, e.g., contain an alcohol such as ethanol or isopropanol and, optionally, an oil. Exemplary gelling agents include crosslinked acrylic acid polymers such as the "carbomer" family of polymers, e.g., carboxypolyalkylenes that may be obtained commercially under the Carbopol® trademark. Also useful are hydrophilic polymers such as polyethylene oxides, polyoxyethylene-polyoxypropylene copolymers and polyvinylalcohol; cellulosic polymers such as hydroxypropyl cellulose, hydroxyethyl cellulose, hydroxypropyl methylcellulose, hydroxypropyl methylcellulose phthalate, and methyl cellulose; gums such as tragacanth and xanthan gum; sodium alginate; and gelatin. In order to prepare a uniform gel, dispersing agents such as alcohol or glycerin can be added, or the gelling agent can be dispersed by trituration, mechanical mixing or stirring, or combinations thereof.

Lotions are preparations generally applied to the skin surface so as to avoid high friction, and are typically liquid or semiliquid preparations in which solid particles, including the active agent, are present in a water or alcohol base. Lotions are usually suspensions of solids, and, e.g., comprise a liquid oily emulsion of the oil-in-water type. Lotions can be used to large body areas, because of the ease of applying a generally fluid composition. It is generally necessary that the insoluble matter in a lotion be finely divided. Lotions will typically contain suspending agents to produce better dispersions as well as compounds useful for localizing and holding the active agent in contact with the skin, e.g., methylcellulose, sodium carboxymethyl-cellulose, or the like.

Ointments are semi-solid preparations that are typically based on petrolatum or other petroleum derivatives. The specific ointment base to be used is one that will provide for optimum active ingredient delivery, and other desired characteristics, e.g., emolliency. As with other carriers or vehicles, an ointment base should be inert, stable, nonirritating and nonsensitizing. Ointment bases may be grouped in four classes: oleaginous bases, emulsifiable bases, emulsion bases and water-soluble bases. Oleaginous ointment bases include, e.g., vegetable oils, fats obtained from animals, and semisolid hydrocarbons obtained from petroleum. Emulsifiable ointment bases, also known as absorbent ointment bases, contain little or no water and include, e.g., hydroxystearin sulfate, anhydrous lanolin and hydrophilic petrolatum. Emulsion ointment bases are either water-in-oil (W/O) emulsions or oil-in-water (O/W) emulsions, and include, e.g., cetyl alcohol, glyceryl monostearate, lanolin and stearic acid. For example, water-soluble ointment bases are prepared from polyethylene glycols of varying molecular weight.

Pastes are semisolid dosage forms in which the active agent is suspended in a suitable base. Depending on the nature of the base, pastes are divided between fatty pastes or those made from single-phase aqueous gels. The base in a fatty paste is generally petrolatum or hydrophilic petrolatum or the like. The pastes made from single-phase aqueous gels generally incorporate carboxymethylcellulose or the like as a base.

Suspensions may be defined as a coarse dispersion containing finely divided insoluble material suspended in a liquid medium.

Formulations may also be prepared with liposomes, micelles, and microspheres.

Various additives may also be included in formulations, e.g. to solubilize the active ingredients. Other optional additives include opacifiers, antioxidants, fragrances, colorants, gelling agents, thickening agents, stabilizers, surfactants and the like.

These and other compositions or formulations suitable for carrying and delivering compounds of Formula I are described in Chapters 22, 39, 43, 45, 50 and 55 of *Remington*, above, which are hereby incorporated by reference in their entireties.

The concentration of compounds of Formula I (which include compounds of Formulae IA, IB, IC, ID, IE, IF and IG) or their salts in compositions, formulations, and dosage forms may be up to the saturation concentration of those compounds (or salts), e.g., up to about 1 M (molar), up to about 500 mM (millimolar), or up to about 150 mM. For example, compositions of the present application can comprise a a concentration of a compound of Formula I (or its salt) ranging from about 0.001 mM to about 1 M, from about 0.01 mM to about 500 mM, from about 0.05 mM to about 150 mM, from about 0.1 mM to about 10 mM, and about 0.5 mM to about 2 mM. Compositions of the present application can also have a concentration of compounds of Formula I or their salts ranging from about 0.1 µg/ml to about 300 g/L, about 3 µg/ml to about 150 g/L, from about 5 µg/ml to about 45 g/L, from about 10 µg/ml to about 3000 µg/ml and about 50 µg/ml to about 600 µg/ml. In a further aspect, compositions of the present application comprise isotonic or physiologically balanced solutions of compounds of Formula I or their salts.

In certain embodiments, the compositions in the form of solutions are osmotically balanced. In further embodiments, the compositions described herein have a therapeutic index ranging from about 10 to about 10,000, e.g. from about 100 to about 1000.

The compounds of Formula I, or their salts, are useful in methods of preventing or treating microbial (e.g. bacterial, viral, or fungal) infection or contamination. Compounds described herein may also be administered to prevent or treat a disease, disorder, ailment, or other pathology caused by bacteria, fungus, virus, or associated biofilm. The compounds or salts described herein may also be used for the preparation of a medicine for the prevention or treatment of microbial infection, contamination or activity in a subject. Such methods comprise administering or applying an effective amount of the compound or salt thereof in or near the area of interest, e.g. in or near a tissue or organ, to a surface of a medical device, within a storage container, and so on.

Compositions of the present application are useful in a wide range or applications in which antimicrobial properties are desirable. Such applications include, without limitation, treatment or reduction of pathogens on or in the skin, nails, hair, or mucous membranes, wounds, surgical sites, and so forth. Applications and areas of interest include wounds, burns, ulcers, inflammation or lesions of the skin, the eyes, ears, nasal passages, sinus, bronchpulmonary system, vagina, rectum and other mucous membranes or related tissues. Applications include treatment of viral conditions such as cold sores, warts, and molluscum contagiosum; dermatological bacterial conditions such as acne, impetigo, cellulitis, erysipelas, cutaneous abcesses, folliculitis, furuncles (boils), and paronychial infections; the treatment of various fungal infections such as onychomycosis (fungal nail infections on fingers and toes); acute or chronic rhinosinusitis or other infections such as otitis, dermatitis, bronchitis, pneumonias such as *Pneumocystis carinii*, fungal infections of urinary, reproductive or sex organs such as vulvovaginal candidosis, colpitis, endometritis, balanitis; infections of the gastrointestinal tract such as stomatitis, oesophagitis, enteritis, or fungal infections of the urethra such as pyelonephritis, ureteritis, cystitis, or urethritis (including, e.g., urinary tract infection, such as catheter-associated urinary tract infection ("CAUTI"); use in lavage, reduction of infectious load in organs for transplantation; reduction of bacterial load in autologous or artificial tissue transplantation; cleaning of tissue sites (e.g., pre- and post-operative surgical preparation); ophthalmic applications (e.g. treatment of viral or bacterial conjunctivitis, cleaning solutions or irrigation of the eye, and, e.g., treatment of tissue before, during, or after ophthalmic surgery); nasal or nasopharyngeal applications including, but not limited to, the treatment of rhinosinusitis or rhinitis caused by viral, bacterial or fungal infections; dental applications including oral disinfection, the treatment of gingivitis or periodontitis; reduction of pathogens in pulmonary infections; treatment of biofilm (e.g. for cystic fibrosis or other diseases that produces biofilms); and animal health applications (e.g. treatment of mastitis). Administration of compositions for these applications may be topical, e.g., topical application to the skin or mucous membranes (e.g. the mouth, nose, eye, ear, vagina, rectum).

Applications also include use in vaccine formulations (as preservative and potentially adjuvant), viral inactivation of both DNA and RNA classes of viruses including HIV, hepatitis A, respiratory syncytial virus, rhinovirus, adenovirus, West Nile virus, HSV-1, HSV-2, SARS, influenza and parainfluenza viruses, picornaviruses, and vaccinia virus (as a model for poxviruses).

Furthermore, the compositions described herein have antimicrobial activity against many other microorganisms, including *Haemophilus influenzae, Escherichia coli, Enterococcus faecium, Enterococcus faecalis, Listeria monocytogenes, Staphylococcus aureus*, methicillin-resistant *S. aureus* (MRSA), *Staphylococcus epidermidis, Streptococcus pneumoniae, Pseudomonas aeruginosa, Proteus mirabilis, Klebsiella pneumoniae, Lactobacillus, Acinetobacter junii*, yeast, including *Candida albicans*, vancomycin-resistant *enterococcus*, molds, and spores, including spores of anthrax and cysts of Acanthamoeba. Vancomycin-resistant enterococci and staphylococci, MRSA, and others can be destroyed by the compositions of the present application. Examples of bacteria implicated in periodontal disease and destroyed by the compositions of the present application are *Bacteroides gingivalis, Bacillus intermedius, Actinomyces actinomycetemcomitans* and *Bacteroides forsythus*. Examples of bacteria that are implicated in mastitis (infection of cow udder) and killed by the compositions are *Streptococcus agalactiae* and *Streptococcus infantarius*. The compositions destroy biofilms and are therefore effective against micro-organisms growing in both planktonic form and in biofilms.

While N-halogenated compounds of Formula I may have inherent antimicrobial activity, the corresponding N-protonated (i.e. non-halogenated) analogs may also have antimicrobial activity, or may be activated to an antimicrobial (or increased antimicrobial) state by a source of halogen. For example, it is well known that hypochlorite and/or hypochlorous acid is generated by neutrophils, eosinophils, mononuclear phagocytes, and B lymphocytes [see, e.g., L. Wang et al., *J. Burns Wounds*, 6, 65-79 (2007) and M. Nagl et al., *Antimicrob. Agents Chemother.* 44(9) 2507-13 (2000)]. Certain organic cloramines, including N-chlorotaurine, have been detected in the supernatants of stimulated granulocytes, and are thought to prolong the oxidative capacity of these cells during oxidative burst and to protect cells from damage by $HOCl/OCl^-$. In a similar fashion to taurine, N-protonated compounds of Formula I in or near these cells may be chlorinated during oxidative burst, and may serve a similar microbicidal and/or protective effect. Thus, compounds of Formula I may be used in methods to generate antimicrobial activity in situ, to prolong or otherwise modulate the oxidative capacity of cells during oxidative burst, or to decrease associated cyctotoxicity.

The compounds described herein may also be useful in a method to treat, disinfect, or decontaminate surfaces or areas, including to kill or reduce or inhibit the growth of bacteria, fungi or viruses, the method comprising the administration of an effective amount of the compound or salt thereof to the surface. Applications include the elimination or reduction of pathogens on or in medical (including surgical, dental, optical, and other) devices, equipment and instruments, (e.g. breathing tubes, catheters, contact lenses, dental implants and equipment, equipment used for organ preservation, hearing aids, prostheses, stents, etc.), devices, food (e.g., meats, fish, fruits, vegetables, nuts, etc.) and food contact surfaces (e.g. cutting tools, storage rooms or containers, etc.) including the elimination or reduction of bacterial biofilms, and agricultural uses including protection of seed stocks.

By way of example, compositions of the present application may be applied to tissues such as the skin directly, via an applicator, aerosol or spray, or incorporated into bandages or wound dressings. The compositions, which may be in the form of solutions, pastes, creams, gels or lotions, and may be used in combination with specially designed bandages in a wound treatment protocol. For example, a bandage may include (or be impregnated with) a gauze, gel, ointment, or similar means to allow the antimicrobial composition to contact the area of interest, e.g. the wound or infection. A bandage may also include an opening or "window" through which topical treatment materials such as the solution of the present application may be applied, reapplied, circulated, etc. The compositions may also be applied in applications (e.g. treatment of burns) where it is desirable to maintain a moist and sterile environment without disturbing the dressing. In one such example, a perforated tube is placed between the dressing and the outer bandage or wrap. Periodically, the composition is passed through the tube thus irrigating the dressing with fresh antimicrobial solution.

In another example, compounds and compositions of the present application may be used for the eradication of bacteria (including bacteria in a biofilm), such as, but not limited to, bacterial and biofilms in or on medical devices, e.g. in the lumen of a catheter (e.g. urinary, central venous, hemodialysis catheters and the like), stent, breathing tube, etc. Such methods may include the destruction of the corresponding biofilm matrix to clear the bacterial load from the medical device, such as improving or maintaining patency in the lumen of a catheter, stent, or breathing tube. Biofilms are a group of microorganisms attached to a substrate and are often associated with the excretion of extracelullar polymeric substance [R. M. Donlan et al., Clin. Microbiol. Rev., 4, 167-193 (2002)]. The demonstrated resistance of biofilms to antimicrobials has caused problems in human health and has had a significant impact on the success of medical implants, e.g., catheters [J. W. Costerton et al., Science, 284(5418), 1318-22 (1999)]. Once catheters are colonized, biofilms will develop on the outer and inner surfaces and cause infections. Reduction of the bacterial load by prevention of the formation of biofilm [J. F. Williams and S. D. Worley, J. Endourology, 14(5), 395-400 (2000); K. Lewis and A. M. Klibanov, Trends in Biotech., 23, 7, 343-348 (2005)], destruction of an existing biofilm [P. Wood et al., Appl. Env. Microb. 62(7), 2598-2602 (1996)] and killing bacteria in biofilm [P. Gilbert and A. J. McBain, Am. J. Infect. Control, 29, 252-255 (2001)] are strategies towards lowering microbial load and reducing biofilm-related infection from any catheters and shunts, such as but not limited to, urinary and central venous catheters, implanted artificial joints, implanted artificial hearts, gastric feeding tubes, and colostomy tubes.

Compounds described herein may be used to treat, eradicate, or prevent the formation of biofilm formed by a variety of bacteria and fungi, including, but not limited to, gram-positive cocci, gram-negative rods, P. aeruginosa, C. albicans, S. aureus, B. cepacia, E. coli, S. epidermidis, A. hydrophila, H. influenzae, S. liquifaciens, P. mirabilis, K. pneumoniae, and P. vulgaris. A discussion of these, and examples of other, biofilm-forming species may be found in, e.g., S. Kjelleberg, and S. Molin, Curr Opin Microbiol., June 5(3):254-8 (2002); J. W. Consterton et al., Science, 284, May 21, 1318-11 (1999); and D. J. Stickler et al., Methods in Enzymology, 310: 494-501 (1999).

In another application of decontaminating or cleaning medical devices, a solution of a compound of the present application may be used to cleanse contact lenses. Such solutions may also contain additional preservatives and disinfecting agents as well as cleaning and other agents. These solutions may be used to store contact lenses (e.g., in packaging, between uses, in carrying cases, etc.), to condition lenses, to wet or re-wet lenses before insertion into the eye, or to clean and rinse lenses. Disinfection of contact lenses is important in the prevention of infections of the eye caused by microorganisms. Microbes are primarily introduced to the eye by handling of the lens. For example, introduction of E. coli may lead to infections of various eye structures, such as microbial keratitis. Fungal pathogens, such as Fusarium, can also infect the eye when transferred from a colonized contact lens. [See, e.g., J. K. Suchecki et al., Ophthalmol. Clin. North Am., 16(3), 471-84 (2003).]

EXAMPLES

The following nonlimiting examples are offered for further illustration.

Example 1

1-(3-chloro-1,4-dimethyl-2,5-dioxoimidazolidin-4-yl)-N,N,N-trimethylmethanaminium chloride (Compound 22-27)

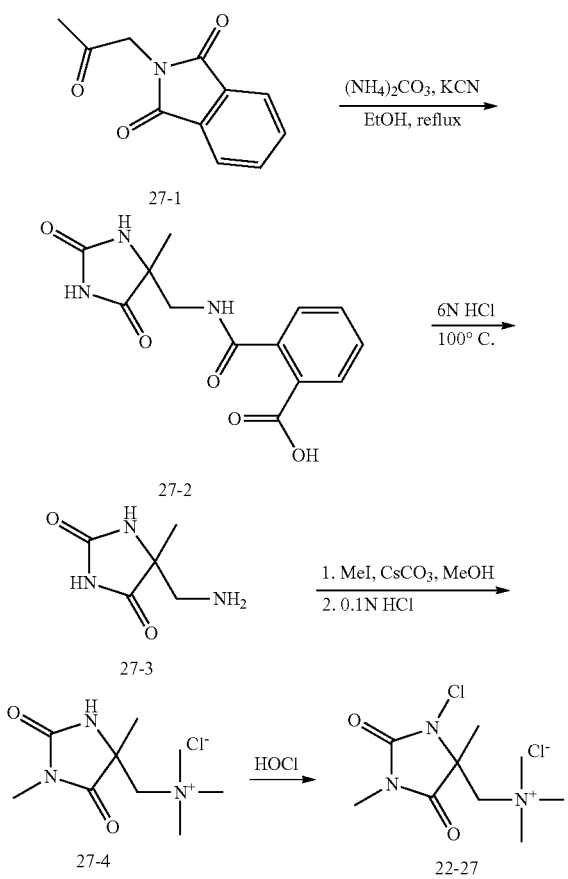

2-((4-Methyl-2,5-dioxoimidazolidin-4-yl)methylcarbamoyl)benzoic acid

Phthalimido acetone (27-1) (14.21 g, 70 mmol, 1 eq.), ammonium carbonate (23.5 g, 245 mmol, 3.5 eq), potassium cyanide (6.8 g, 105 mmol, 1.5 eq.) in EtOH (70 mL) and H₂O (70 mL) were heated at 75° C. for 18 h in a sealed tube. The reaction mixture was cooled to room temperature and the volatiles were evaporated in vacuo. The reaction mixture was partitioned between ethyl acetate (150 mL) and H₂O (100 mL). The aqueous phase was adjusted to pH 4 and extracted with more ethyl acetate (2×150 mL). Organic layers were combined, dried (MgSO₄) and concentrated in vacuo to yield the crude product (27-2), which was directly used in the next step. Yield: 12.33 g (61%). ¹H-NMR (400 MHz, CD₃OD-d₄) δ 7.60-7.41 (m, 4H), 3.70 (d, 1H), 3.56 (d, 1H), 1.44 (s, 3H). LCMS—[M+H] m/z 292.

5-(Amino methyl)-5-methylimidazolidine-2,4-dione

To a portion of hydantoin amide 27-2 (2.2 g, 7.5 mmol, 1 eq.) was added 6 N HCl (110 mL), and the reaction mixture was heated at 100° C. for 18 h. The reaction mixture was cooled to room temperature and the volatiles were removed in vacuo. The resulting residue was triturated with diethyl ether to afford the product 27-3 as a white solid. Yield: 1.63 g (100%). LCMS—[M+Na] m/z 167.

1-(1,4-Dimethyl-2,5-dioxoimidazolidin-4-yl)-N,N,N-trimethylmethanaminium chloride To hydantoin amine 27-3 (1.63 g, 7.5 mmol, 1 eq.) at 5° C. was added cesium carbonate (7.46 g, 22.9 mmol, 3 eq) followed by methyl iodide (4.27 mL, 68.4 mmol, 9 eq) and the reaction was stirred at room temperature for 72 h. The reaction mixture was diluted with methanol (30 mL) and passed through a silica gel (SiO₂) pad. The filtrate was concentrated in vacuo and purified by column chromatography (20-30% methanol in dichloromethane). The product obtained was stirred in 0.1 N HCl and lyophilized to yield a white solid (27-4). Yield: 712 mg (47%). ¹H-NMR (400 MHz, D₂O) δ 4.00 (d, 1H), 3.77 (d, 1H), 3.19 (s, 9H), 3.07 (s, 3H), 1.52 (s, 3H). LCMS—[M] m/z 199.

1-(3-Chloro-1,4-dimethyl-2,5-dioxoimidazolidin-4-yl)-N,N,N-trimethylmethanaminium chloride To a portion of trimethyl ammonium hydantoin 27-4 (80 mg, 0.34 mmol, 1 eq.) in H₂O (5 mL) at 5° C. was added HOCl (254 μL, 0.17 mmol, 0.5 eq.) and the reaction was stirred for 2 h at 5° C. The reaction mixture was concentrated in vacuo and purified by prep HPLC (gradient from 5% to 95% MeOH in H₂O; 20 mL/min flow rate; C₁₈ Restek column) to yield Compound 22-27 as a pure product. Yield: 45 mg (50%). ¹H-NMR (400 MHz, D₂O) δ 4.08 (d, 1H), 3.95 (d, 1H), 3.21 (s, 9H), 3.16 (s, 3H), 1.61 (s, 3H). LCMS—[M] m/z 234.

Example 2

1,3-Dichloro-8,8-dimethyl-2,4-dioxo-1,3-diaza-8-azoniaspiro[4.5]decane (Compound 22-37)

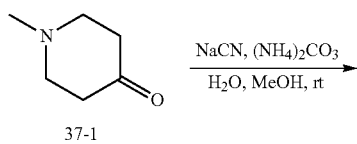

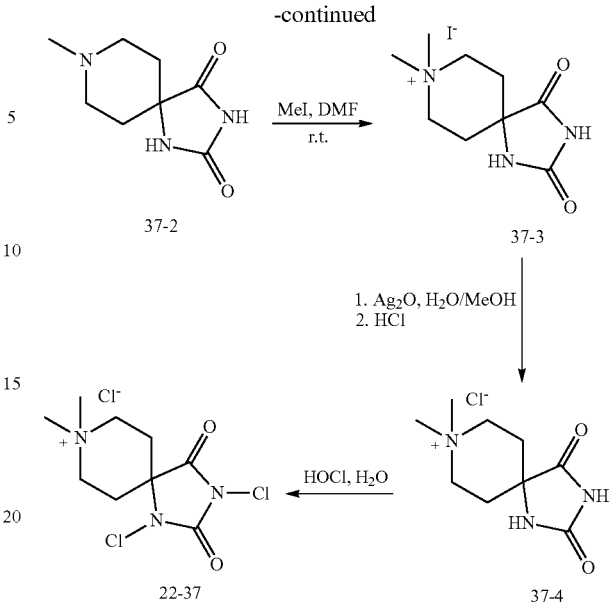

8-Methyl-1,3,8-triazaspiro[4,5]decane-2,4-dione

1-Methyl-4-piperidone (37-1) (10.0 g, 88.5 mmol, 1 eq.), ammonium carbonate (29.7 g, 309.7 mmol, 3.5 eq), potassium cyanide (8.6 g, 132.7 mmol, 1.5 eq.) in MeOH (80 mL) and H₂O (80 mL) were stirred at 23° C. for 48 h. The reaction mixture was heterogeneous with a white solid suspension, which was filtered out and washed with H₂O (2×150 mL). The filtered white solid was obtained as the product (37-2). Yield: 8.2 g (51%). ¹H-NMR (400 MHz, CD₃OD) δ 2.85 (m, 2H), 2.34 (m, 2H), 2.32 (s, 3H), 2.05 (m, 2H), 1.68 (m, 2H). LCMS—[M+H] m/z 184.

8,8-Dimethyl-2,4-dioxo-1,3-diaza-8-azoniaspiro[4,5]decane iodide

A portion of hydantoin 37-2 (1.0 g, 5.5 mmol, 1 eq.) was dissolved in DMF (15 mL). To this white suspension was added more DMF until the mixture was nearly homogeneous. This solution was cooled to 5° C. and methyl iodide (340 μL, 5.46 mmol, 1 eq) was added while stirring at room temperature. The homogeneous suspension became a white cloudy heterogeneous suspension over time. The mixture was stirred overnight and a white solid was filtered out from the suspension, then washed with DMF (50 mL) and dichloromethane (50 mL). The product (37-3) was obtained as a white solid. Yield: 1.08 g (100%). LCMS—[M] m/z 198.

8,8-Dimethyl-2,4-dioxo-1,3-diaza-8-azoniaspiro[4,5]decane chloride

To hydantoin iodide salt 37-3 (1.08 g, 5.5 mmol, 1 eq.) in H₂O (35 mL) was added silver oxide (2.33 g, 10.1 mmol, 2 eq) in one portion to give a black suspension. The reaction mixture was stirred for 1 h and filtered through celite. The filtrate was acidified to pH 2 by adding 2 N HCl and this solution was filtered through celite, washing with H₂O (35 mL). The filtrate was concentrated to a pale yellow oil (37-4). Yield: 712 mg (47%). ¹H-NMR (400 MHz, D₂O) δ 3.79 (m, 2H), 3.54 (m, 2H), 3.25 (s, 6H), 2.42 (m, 2H), 2.23 (m, 2H). LCMS—[M] m/z 198.

1,3-Dichloro-8,8-dimethyl-2,4-dioxo-1,3-diaza-8-azoniaspiro[4,5]decane chloride To a portion of dimethyl ammonium hydantoin 37-4 (80 mg, 0.34 mmol, 1 eq.) in H$_2$O (5 mL) at 5° C. was added HOCl (254 µL, 0.17 mmol, 0.5 eq.) and the reaction was stirred for 2 h at 5° C. The reaction mixture was concentrated in vacuo and purified by prep HPLC (gradient from 5% to 95% MeOH in H$_2$O; 20 mL/min flow rate; C$_{18}$ Restek column) to yield 1,3-dichloro-8,8-dimethyl-2,4-dioxo-1,3-diaza-8-azoniaspiro[4.5]decane Compound 22-37as a pure product. Yield: 45 mg (50%). $^1$H-NMR (400 MHz, D$_2$O) δ 3.92 (m, 2H), 3.71 (m, 2H), 3.32 (s, 3H), 3.27 (s, 3H) 2.70 (m, 2H), 2.30 (m, 2H). LCMS—[M] m/z 266.

Example 3

3-chloro-8,8-dimethyl-2-oxo-1-oxa-3-aza-8-azoniaspiro[4.5]decane chloride (Compound 22-36)

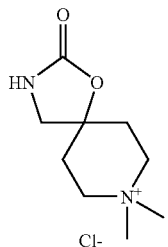

8,8-Dimethyl-2-oxo-1-oxa-3-aza-8-azoniaspiro[4.5] decane chloride

1-Oxa-3,8-diazaspiro[4.5]decan-2-one hydrochloride (1.23 g, 6.38 mmol), which was prepared as per Smith, P. W., et. al. *J. Med. Chem.* 1995, 38, 3772-3779, was dissolved in N,N-dimethylformamide (60 ml). Methyl iodide (30 ml) and cesium carbonate (5.11 g, 15.68 mmol) was added to the solution, and the combined mixture was stirred at room temperature for 18 hours. The reaction mixture was concentrated in vacuo, and water was added (200 ml). Silver(I) oxide (10 g) was added, and the aqueous solution was stirred for 1 hour. The mixture was filtered, and the resulting solution was acidified to pH 1 with 2N hydrochloric acid. The acidic solution was filtered again, and the aqueous mixture was concentrated to give 1.63 g (92%) of 8,8-dimethyl-2-oxo-1-oxa-3-aza-8-azoniaspiro[4.5]decane chloride. $^1$H NMR (CDCl$_3$) δ3.49-3.68 (m, 6H), 3.25 (s, 3H), 3.18 (s, 3H), 2.25-2.41 (m, 4H); MS(ESI+) calculated for C$_9$H$_{17}$N$_2$O$_2$: 185.13, Found: 185 (M+).

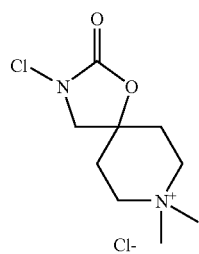

3-Chloro-8,8-dimethyl-2-oxo-1-oxa-3-aza-8-azoniaspiro[4.5]decane chloride 8,8-Dimethyl-2-oxo-1-oxa-3-aza-8-azoniaspiro[4.5]decane chloride (1.60 g, 7.25 mmol) was dissolved in methanol (80 ml). t-Butylhypochlorite (1.18 g, 10.87 mmol) was added to the solution, and the combined mixture was stirred for 1 hour at room temperature. The reaction mixture was monitored by HPLC-MS. The reaction mixture was concentrated in vacuo. The crude material was purified by Prep-HPLC to give 243 mg (13%). $^1$H NMR (CDCl$_3$) δ 3.84 (s, 2H), 3.52-3.69 (m, 4H), 3.25 (s, 3H), 3.18 (s, 3H), 2.32-2.46 (m, 4H); MS(ESI+) calculated for C$_9$H$_{16}$ClN$_2$O$_2$: 219.09, Found: 219 (M+).

Example 4

3-Chloro-4-methyl-4-(methylsulfonic acid)oxazolidin-2-one (Compound 22-01)

2-(tert-Butoxycarbonylamino)-2-methylpropane-1,3-diol

A solution of 2-amino-2-methylpropane-1,3-diol (7.66 g, 72.7 mmol) and triethylamine (10 ml, 72 mmol) in CH$_2$Cl$_2$ (100 ml) was cooled to 0° C. and Boc$_2$O (16.59 g, 76.0 mmol) in CH$_2$Cl$_2$ (50 ml) was added dropwise over 30 min. The solution was stirred for 28 h, evaporated, and dissolved in EtOAc (20 ml). The solution precipitated large, white block crystals overnight (10.42 g) and cooling to −20° C. for 24 h yielded a second crop of small, white, quartz-shaped crystals (0.96 g). Both portions were analytically identical, and were pooled to give the titled compound (11.38 g, 55.51 mmol, 76.4%) as a white solid. 1H NMR (CDCl$_3$) δ 1.17 (s, 3H), 1.43 (s, 9H), 3.49 (br s, 2H), 3.62 (dd, 2H, J=6.8, 11.2 Hz), 3.78 (dd, 2H, J=5.6, 11.2 Hz), 4.98 (s, 1H). m/z expected for C$_9$H$_{19}$NNaO$_4$+: 228.1; found 228.1.

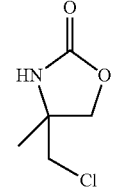

4-Methyl-4-chloromethyloxazolidin-2-one

A solution of 2-(tert-butoxycarbonylamino)-2-methyl-1,3-propanediol (2.28 g, 11.1 mmol) in CH$_2$Cl$_2$ (100 ml) and pyridine (2.0 ml, 25 mmol) was cooled to 0° C. and sulfuryl chloride (1.0 ml, 12 mmol) in CH$_2$Cl$_2$ (20 ml) was added dropwise over 15 min. The solution was warmed to RT over 4 h, diluted with diethyl ether (300 ml), washed with 3× 100 ml 5% NaHSO$_4$, 3× 100 ml sat. NaHCO$_3$, 1× 100 ml sat. NaCl, dried on MgSO$_4$, and evaporated. The crude material was purified by flash chromatography (30-100% EtOAc in hexanes) to afford the title compound as a clear oil (470 mg, 3.14 mmol, 28.3%). $^1$H NMR (CDCl$_3$, 400 MHz) δ 1.49 (s, 3H), 3.55 (s, 2H), 4.12 (d, 1H, J=9.2 Hz), 4.33 (d, 1H, J=8.8 Hz), 5.9 (br s, 1H). APCI/ESI calculated for C$_5$H$_8$ClNO$_2$: 149.02. Found: 150 (MH+).

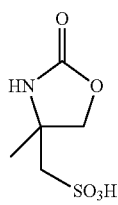

4-Methyl-4-(methylsulfonic acid)oxazolidin-2-one

To a solution of 4-methyl-4-chloromethyloxazolidin-2-one (440 mg, 2.77 mmol) in 1,4-dioxane (3 ml) was added $Na_2SO_3$ (500 mg, 4.68 mmol) in $H_2O$ (3 ml). The solution was heated to 50° C. for 14 h, cooled to RT, and evaporated. The crude material was suspended in MeOH, filtered through a medium glass frit, then through a 0.2 mm nylon filter. The filtrate was evaporated and used without further purification. APCI/ESI calculated for $C_5H_9NO_5S$: 195.02. Found: 194 (M−H+).

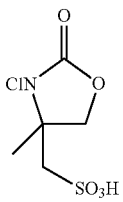

3-Chloro-4-methyl-4-(methylsulfonic acid)oxazolidin-2-one

To a suspension of 4-methyl-4-(methylsulfonic acid)oxazolidin-2-one (2.77 mmol) in MeOH (3 ml) was added tert-butylhypochlorite (500 ul, 4.19 mmol). The solution was stirred for 2 h, evaporated, and the crude material was purified by preparatory HPLC ($H_2O$/$CH_3CN$) to afford the title compound as a clear oil. $^1$H NMR ($D_2O$, 400 MHz) δ 1.54 (s, 3H), 3.26 (d, 1H, J=14.8 Hz), 3.40 (d, 1H, J=15.2 Hz), 4.39 (d, 1H, J=9.2 Hz), 5.00 (d, 1H, J=8.8 Hz). APCI/ESI calculated for $C_5H_8ClNO_5S$: 228.98. Found: 228 (M−H+).

Example 5

1-(3-Chloro-4-methyl-2-oxooxazolidin-4-yl)-N,N,N-trimethylmethanaminium chloride (Compound 22-04)

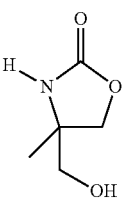

4-(Hydroxymethyl)-4-methyloxazolidin-2-one

A flask with 2-amino-2-methyl-1,3-propanediol (3.32 g, 31.6 mmol) and diethyl carbonate (10 ml, 83 mmol) was fitted with a Dean-Stark trap and condenser and the suspension heated to 140° C. until 5 ml of liquid had been collected in the trap (~8 hr). The solution was cooled to RT slowly, and the resulting white, block crystals were filtered off (2.79 g, 21.3 mmol, 67%). The supernatant was purified by flash chromatography to afford the title compound as a white solid (1.04 g, 7.94 mmol, 25%). $^1$H NMR ($CDCl_3$, 400 MHz) δ 1.36 (s, 3H), 2.2 (br s, 1H), 3.56 (m, 2H), 4.06 (d, J=8.8 Hz, 1H), 4.33 (d, J=8.8 Hz, 1H), 5.2-5.3 (br s, 1H). ESI/APCI calculated for $C_5H_9NO_3$: 131.06. Found: 132 (MH+).

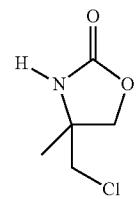

4-(Chloromethyl)-4-methyloxazolidin-2-one

To a suspension of 4-(hydroxymethyl)-4-methyloxazolidin-2-one (1.89 g, 14.4 mmol) in 1,2-dichloroethane (10 ml) was added thionyl chloride (5.0 ml, 69 mmol) dropwise over 10 min. Pyridine (5.0 ml, 62 mmol) was added, and the solution heated to 110° C. for 2 h. The solution was cooled to RT, concentrated, and the residue purified by flash chromatography (30%→100% EtOAc in hexanes) to give the title compound as a white solid (1.52 g, 10.2 mmmol, 71%). $^1$H NMR ($CDCl_3$, 400 MHz) δ 1.49 (s, 3H), 3.55 (s, 2H), 4.12 (d, J=9.2 Hz, 1H), 4.33 (d, 8.8 Hz, 1H), 5.8 (br s, 1H). ESI/APCI calculated for $C_5H_8ClNO_2$: 149.02. Found: 150 (MH+).

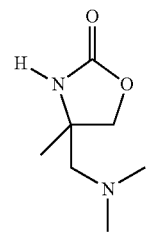

4-((Dimethylamino)methyl)-4-methyloxazolidin-2-one

A solution of 4-(chloromethyl)-4-methyloxazolidin-2-one (2.97 g, 19.9 mmol) in 2.0 M dimethylamine in THF (50 ml, 100 mmol) in a sealed tube was heated to 85° C. for 24 h, cooled to RT, and filtered through a coarse glass filter to remove precipitated dimethylammonium chloride. The filtrate was concentrated, and the residue purified by flash chromatography (3%→10% MeOH in $CH_2Cl_2$) to afford the oxazolidinone as a brown oil (1.02 g, 6.45 mmol, 32%), and the dihydrooxazole as a yellow oil (1.62 g, 10.2 mmol, 52%). $R_f$=0.5 in 10% MeOH in $CH_2Cl_2$. $^1$H NMR ($CDCl_3$, 400 MHz) δ 1.35 (s, 3H), 2.33 (s, 6H), 2.37 (d, J=13.6 Hz, 1H), 2.43 (d, J=14.4 Hz, 1H), 4.02 (d, J=8.4 Hz, 1H), 4.18 (d, J=8.4 Hz, 1H), 5.2 (br s, 1H). ESI/APCI expected for $C_7H_{14}N_2O_2$: 158.11. Found: 159 (MH+).

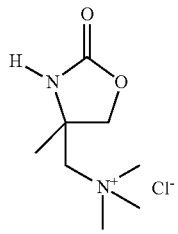

N,N,N-Trimethyl-1-(4-methyl-2-oxooxazolidin-4-yl)methanaminium chloride

To a solution of 4-((dimethylamino)methyl)-4-methyloxazolidin-2-one (240 mg, 1.52 mmol) in MeOH (1 ml) was added methyl iodide (1.0 ml, 16 mmol). The solution was stirred for 3 h and concentrated. The residue was redissolved in H$_2$O (2 ml), and Ag$_2$O (200 mg, 0.86 mmol) was added. The solution was stirred for 5 min, filtered through PTFE (0.45 um), and the cloudy suspension treated with 6 M HCl (~200 uL) until the pH was 7. The suspension was filtered through PTFE again, evaporated, and used crude. ESI/APCI expected for C$_8$H$_{17}$N$_2$O$_2^+$: 173.13. Found: 173 (M$^+$).

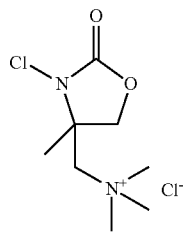

1-(3-Chloro-4-methyl-2-oxooxazolidin-4-yl)-N,N,N-trimethylmethanaminium chloride To a solution of N,N,N-trimethyl-1-(4-methyl-2-oxooxazolidin-4-yl)methanaminium chloride (1.52 mmol) in MeOH (1 ml) was added, dropwise, tert-butylhypochlorite (250 uL, 2.10 mmol). The solution was stirred for 3 h, evaporated, and purified by preparatory HPLC (H$_2$O/CH$_3$CN) to afford the title compound as a yellow foam (115.6 mg, 0.475 mmol, 31% over two steps). $^1$H NMR (D$_2$O, 400 MHz) δ 1.64 (s, 3H), 3.31 (s, 9H), 3.80 (d, J=15.2 Hz, 1H), 3.88 (d, J=14.8 Hz, 1H), 4.61 (d, J=9.6 Hz, 1H), 4.93 (d, J=10.0 Hz, 1H). ESI/APCI expected for C$_8$H$_{16}$ClN$_2$O$_2^+$: 207.09. Found: 207 (M$^+$).

Example 6

N-((3-chloro-4-methyl-2-oxooxazolidin-4-yl)methyl)-N,N-dimethylethanaminium chloride (Compound 22-38)

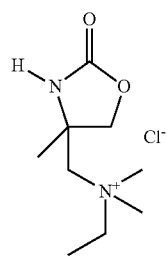

N,N-Dimethyl-N-((4-methyl-2-oxooxazolidin-4-yl)methyl)ethanaminium chloride

A solution of 4-((dimethylamino)methyl)-4-methyloxazolidin-2-one (1.07 g, 6.76 mmol) and ethyl iodide (2.0 ml, 25 mmol) in MeOH (10 ml) in a sealed tube was heated to 70° C. for 16 h, then cooled to RT, and diluted with water (20 ml). Silver (I) oxide (470 mg, 2.03 mmol) was added, then 1.0 M HCl in H$_2$O (ca. 1.5 ml) until the pH of the solution was neutral (6.5). The solution was filtered through Celite, and evaporated. ESI/APCI expected for C$_9$H$_{19}$N$_2$O$_2^+$: 187.14. Found: 187.

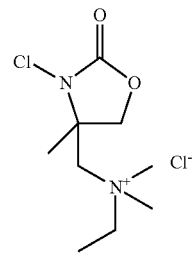

N-((3-Chloro-4-methyl-2-oxooxazolidin-4-yl)methyl)-N,N-dimethylethanaminium chloride To a solution of N,N-dimethyl-N-((4-methyl-2-oxooxazolidin-4-yl)methyl)ethanaminium chloride (6.76 mmol) in MeOH (10 ml) was added, dropwise, tert-butylhypochlorite (1.6 ml, 10 mmol). The solution was stirred for 2 h, evaporated, and purified by preparative HPLC (H$_2$O/MeOH) to afford the title compound as a white foam (667 mg, 2.59 mmol, 38% over two steps). $^1$H NMR (D$_2$O, 400 MHz) δ 1.44 (t, J=7.2 Hz, 3H), 1.65 (s, 3H), 3.22 (s, 3H), 3.25 (s, 3H), 3.57 (q, J=7.2 Hz, 2H), 3.76-3.80 (m, 2H), 4.61 (d, J=9.6 Hz, 1H), 4.90 (d, J=9.6 Hz, 1H). ESI/APCI expected for C$_9$H$_{18}$ClN$_2$O$_2^+$: 221.11. Found: 221.

Example 7

2-((3-Chloro-4-methyl-2-oxooxazolidin-4-yl)methylsulfonyl)ethanesulfonic acid (Compound 22-39)

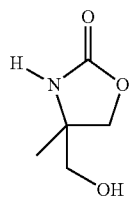

4-(Hydroxymethyl)-4-methyloxazolidin-2-one

A flask with 2-amino-2-methyl-1,3-propanediol (3.32 g, 31.6 mmol) and diethyl carbonate (10 ml, 83 mmol) was fitted with a Dean-Stark trap and condenser and the suspension heated to 140° C. until 5 ml of liquid had been collected in the trap (~8 hr). The solution was cooled to RT slowly, and the resulting white, block crystals were filtered off (2.79 g, 21.3 mmol, 67%). The supernatant was purified by flash chromatography to afford the title compound as a white solid (1.04 g, 7.94 mmol, 25%). $^1$H NMR (CDCl$_3$, 400 MHz) δ 1.36 (s, 3H), 2.2 (br s, 1H), 3.56 (m, 2H), 4.06 (d, J=8.8 Hz, 1H), 4.33 (d, J=8.8 Hz, 1H), 5.2-5.3 (br s, 1H). ESI/APCI calculated for C$_5$H$_9$NO$_3$: 131.06. Found: 132 (MH$^+$).

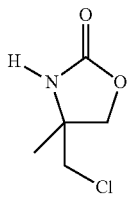

4-(Chloromethyl)-4-methyloxazolidin-2-one

To a suspension of 4-(hydroxymethyl)-4-methyloxazolidin-2-one (1.89 g, 14.4 mmol) in 1,2-dichloroethane (10 ml) was added thionyl chloride (5.0 ml, 69 mmol) dropwise over 10 min. Pyridine (5.0 ml, 62 mmol) was added, and the solution heated to 110° C. for 2 h. The solution was cooled to RT, concentrated, and the residue purified by flash chromatography (30%→100% EtOAc in hexanes) to give the title compound as a white solid (1.52 g, 10.2 mmmol, 71%). $^1$H NMR (CDCl$_3$, 400 MHz) δ 1.49 (s, 3H), 3.55 (s, 2H), 4.12 (d, J=9.2 Hz, 1H), 4.33 (d, 8.8 Hz, 1H), 5.8 (br s, 1H). ESI/APCI calculated for C$_5$H$_8$ClNO$_2$: 149.02. Found: 150 (MH$^+$).

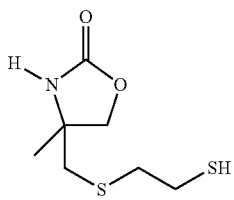

4-((2-Mercaptoethylthio)methyl)-4-methyloxazolidin-2-one

To a solution of 4-(chloromethyl)-4-methyloxazolidin-2-one (1.85 g, 12.4 mmol) in DMF (5 ml) was added 1,2-ethanedithiol (10.0 ml, 119 mmol). Triethylamine (2.0 ml, 14 mmol) was added, and the solution heated to 90° C. for 2 h, then cooled to RT and concentrated in vacuo. Purification of the residue by flash chromatography (30%→80% EtOAc in hexanes) afforded a mixture of the title compound and various EDT disulfide adducts which was used without further purification. ESI/APCI expected for C$_7$H$_{13}$NO$_2$S$_2$: 207.04. Found: 208 (MH$^+$), 300 (MH$^+$+EDT), 414 (MNa$^+$+2 EDT).

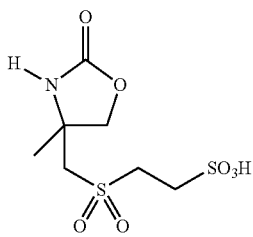 [SMILES: CC1(CS(=O)(=O)CCS(=O)(=O)O)COC(=O)N1]

2-((4-Methyl-2-oxooxazolidin-4-yl)methylsulfonyl)ethanesulfonic acid

To a solution of 4-((2-mercaptoethylthio)methyl)-4-methyloxazolidin-2-one (12.4 mmol) in CH$_2$Cl$_2$ (50 ml) was added ~77% mCPBA (15.5 g, 69.2 mmol) in small portions over 15 min. The solution was stirred for 15 h and then concentrated in vacuo. The residue was suspended in MeOH (10 ml) and filtered, and the filtrate purified by preparatory HPLC (H$_2$O/CH$_3$CN) to give the title compound as a clear oil (1.19 g, 4.14 mmol, 33%). $^1$H NMR (D$_2$O, 400 MHz) δ 1.58 (s, 3H), 3.3-3.4 (m, 2H), 3.6-3.7 (m, 2H), 3.76 (s, 2H), 4.29 (d, J=9.2 Hz, 1H), 4.67 (d, J=10.4 Hz, 1H). ESI/APCI expected for C$_7$H$_{13}$NO$_7$S$_2$: 287.01. Found: 286 (M–H$^+$).

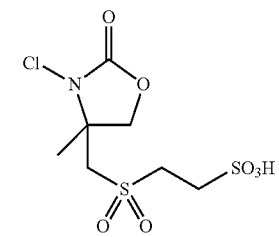 [SMILES: CC1(CS(=O)(=O)CCS(=O)(=O)O)COC(=O)N1Cl]

2-((3-Chloro-4-methyl-2-oxooxazolidin-4-yl)methylsulfonyl)ethanesulfonic acid

To a solution of 2-((4-methyl-2-oxooxazolidin-4-yl)methylsulfonyl)ethanesulfonic acid (950 mg, 3.31 mmol) in MeOH (5 ml) was added, dropwise, tert-butylhypochlorite (500 ul, 4.2 mmol). The solution was stirred for 1 h, concentrated in vacuo, and purified by preparatory HPLC (H$_2$O/MeOH) to afford the title compound as a clear oil (430.0 mg, 1.336 mmol, 40%). $^1$H NMR (D$_2$O, 400 MHz) δ 1.60 (s, 3H), 3.3-3.4 (m, 2H), 3.6-3.7 (m, 2H), 3.80 (d, J=14.8 Hz, 1H), 3.96 (d, J=14.8 Hz, 1H), 4.47 (d, J=9.4 Hz, 1H), 5.05 (d, J=9.4 Hz, 1H). ESI/APCI expected for C$_7$H$_{12}$ClNO$_7$S$_2$: 320.97. Found: 320 (M–H$^+$).

Example 8

N-((3-Chloro-4-methyl-2-oxooxazolidin-4-yl)methyl)-N,N-dimethylpropan-1-aminium chloride (Compound 22-40)

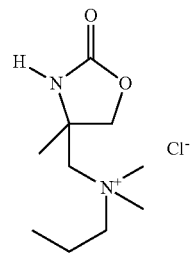

N,N-Dimethyl-N-((4-methyl-2-oxooxazolidin-4-yl)methyl)propan-1-aminium chloride

A solution of 4-((dimethylamino)methyl)-4-methyloxazolidin-2-one (1.03 g, 6.51 mmol) in EtOH (5 ml) was added propyl iodide (2.5 ml, 26 mmol) in a sealed tube was heated to 50° C. for 16 h, then 70° C. for 6 h, then cooled to RT. Potassium carbonate (300 mg, 2.1 mmol) was added, and the solution was heated to 70° C. for an additional 20 h, cooled to RT, and diluted with H$_2$O (10 ml). Silver (I) oxide (850 mg, 3.67 mmol) was added, and stirred for 30 min, and then 6.0 M HCl (~400 ul) added until the solution was pH 7. The suspension was filtered through Celite and evaporated. ESI/APCI expected for $C_{10}H_{21}N_2O_2^+$: 201.16. Found: 201.

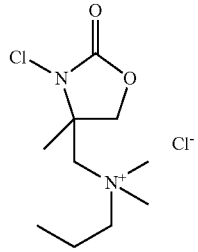

N-((3-Chloro-4-methyl-2-oxooxazolidin-4-yl)methyl)-N,N-dimethylpropan-1-aminium chloride To a solution of N,N-dimethyl-N-((4-methyl-2-oxooxazolidin-4-yl)methyl)propan-1-aminium chloride (6.51 mmol) in MeOH (5 ml) was added, dropwise, tert-butylhypochlorite (~2.5 ml) until the reaction mixture was clear with white precipitate. The solution was filtered through a 0.45 μm nylon filter, then evaporated and purified on preparative HPLC (H$_2$O/MeOH) to afford the title compound as a white foam (248.1 mg, 0.9648 mmol, 15% over two steps). $^1$H NMR (D$_2$O, 400 MHz) δ 0.99 (t, J=7.2 Hz, 3H), 1.64 (s, 3H), 1.8-2.0 (m, 2H), 3.24 (s, 3H), 3.26 (s, 3H), 3.40-3.45 (m, 2H), 3.75 (d, J=15.2 Hz, 1H), 3.82 (d, J=15.2 Hz, 1H), 4.62 (d, J=9.6 Hz, 1H), 4.90 (d, J=9.6 Hz, 1H). ESI/APCI expected for $C_{10}H_{20}ClN_2O_2^+$: 235.12. Found: 235.

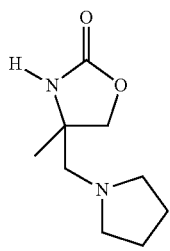

4-Methyl-4-(pyrrolidin-1-ylmethyl)oxazolidin-2-one

To a solution of 4-(chloromethyl)-4-methyloxazolidin-2-one (1.41 g, 9.43 mmol) in THF (40 ml) was added pyrrolidine (5.0 ml, 61 mmol) and sodium iodide (1.03 g, 6.87 mmol). The solution was sealed, heated to 85° C. for 24 h, cooled to RT, filtered, and concentrated in vacuo. Flash chromatography (2%→12% MeOH in CH$_2$Cl$_2$) afforded the oxazolidinone (609.8 mg, 3.31 mmol, 35%) as a brown oil which solidified upon standing. The dihydrooxazole was isolated in roughly 75% purity (1.8 g crude yield) and was characterized only by MS. $^1$H NMR (CDCl$_3$, 400 MHz) δ 1.35 (s, 3H), 1.7-1.8 (m, 4H), 2.5-2.7 (m, 6H), 4.02 (d, J=8.4 Hz, 1H), 4.24 (d, J=8.4 Hz, 1H), 5.3-5.4 (br s, 1H). ESI/APCI expected for $C_9H_{16}N_2O_2$: 184.12. Found: 185 (MH$^+$). $^1$H NMR (CDCl$_3$, 400 MHz) δ 1.35 (s, 3H), 1.7-1.8 (m, 4H), 2.5-2.7 (m, 6H), 4.02 (d, J=8.4 Hz, 1H), 4.24 (d, J=8.4 Hz, 1H), 5.3-5.4 (br s, 1H). ESI/APCI expected for $C_9H_{16}N_2O_2$: 184.12. Found: 185 (MH$^+$).

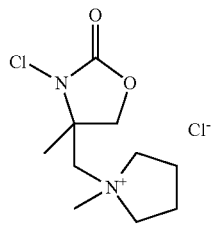

1-Methyl-1-((4-methyl-2-oxooxazolidin-4-yl)methyl)pyrrolidinium chloride

A solution of 4-methyl-4-(pyrrolidin-1-ylmethyl)oxazolidin-2-one (585.7 mg, 3.18 mmol) and methyl iodide (1.2 ml, 19 mmol) in EtOH (4 ml) in a sealed tube was stirred at RT for 15 h, then heated to 70° C. for 6 h. The solution was evaporated, redissolved in 1:1 MeOH:H$_2$O (20 ml), and silver (I) oxide (450 mg, 1.94 mmol) added. The suspension was stirred for 30 min, filtered through Celite, and to the filtrate 6 M HCl (~600 ul) was added until the solution was pH 7. The solution was filtered through Celite, and evaporated. ESI/APCI expected for $C_{10}H_{19}N_2O_2^+$: 199.14. Found: 199.

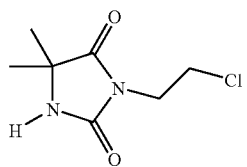

1-(3-Chloro-4-methyl-2-oxooxazolidin-4-yl)methyl)-1-methylpyrrolidinium chloride To a solution of 1-methyl-1-((4-methyl-2-oxooxazolidin-4-yl)methyl)pyrrolidinium chloride (3.18 mmol) in MeOH (5 ml) was added tert-butylhypochlorite (~2.7 ml) until the solution was clear with a white precipitate. The solution was evaporated, and purified by preparative HPLC (H$_2$O/MeOH) to afford the title compound as a white foam (389.2 mg, 1.513 mmol, 48% over two steps). $^1$H NMR (D$_2$O, 400 MHz) δ 1.63 (s, 3H), 2.2-2.3 (m, 4H), 3.17 (s, 3H), 3.5-3.7 (m, 2H), 3.7-3.9 (m, 3H), 3.95 (d, J=14.8 Hz, 1H), 4.62 (d, J=9.6 Hz, 1H), 4.91 (d, J=9.2 Hz, 1H). ESI/APCI expected for $C_{10}H_{18}ClN_2O_2^+$: 233.11. Found: 233.

Example 9

2-(3-Chloro-4,4-dimethyl-2,5-dioxoimidazolidin-1-yl)ethanesulfonic acid (Compound 22-24)

3-(2-Chloroethyl)-5,5-dimethylimidazolidine-2,4-dione 5,5-Dimethylhydantoin (5 g, 39 mmol, 1 eq.) was added to a solution of potassium hydroxide (2.18 g, 39 mmol, 1 eq.) in EtOH (100 mL). 1-bromo-2-chloroethane (11.2 g, 78 mmol, 2 eq.) was added in one portion. The resulting mixture was refluxed overnight. Reaction was cooled to room temperature and concentrated in vacuo. Crude residue was re-suspended in ethyl acetate (150 mL), and washed with H$_2$O (100 mL), saturated aqueous sodium bicarbonate (100 mL) then brine (100 mL). Organic layer was dried (Na$_2$SO$_4$) and concentrated in vacuo to yield the crude product, which was directly used in the next step. Yield: 5.4 g (73%). LCMS—[M+H] m/z 191.

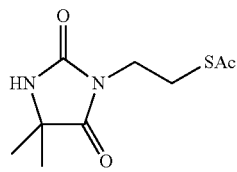

S-2-(4,4-Dimethyl-2,5-dioxoimidazolidin-1-yl)ethyl ethanethioate

To a portion of chloride (950 mg, 5 mmol, 1 eq.) in DMF (15 mL) was added potassium thioacetate (1.14 g, 10 mmol, 2 eq.) and the reaction mixture was heated at 70° C. for 1 h. Reaction was cooled to room temperature and concentrated in vacuo. Crude mixture was re-suspended in ethyl acetate (150 mL) and washed with H$_2$O (50 mL), saturated aqueous sodium bicarbonate (50 mL), then brine (50 mL). Organic layer was dried (Na$_2$SO$_4$) and concentrated in vacuo to yield the crude product as a yellow gum. Purified by column chromatography (50% EtOAc/hexane) to yield pure product. Yield: 890 mg (77%). $^1$H-NMR (400 MHz, CDCl$_3$) δ 3.74 (t, 2H), 3.18 (t, 2H), 2.33 (s, 3H), 1.47 (s, 6H). LCMS—[M+H] m/z 231.

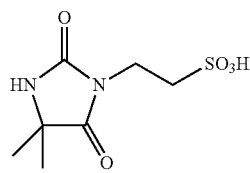

2-(4,4-Dimethyl-2,5-dioxoimidazolidin-1-yl)ethanesulfonic acid

To a portion of thioacetate (445 mg, 1.93 mmol, 1 eq.) was added hydrogen peroxide (30 wt. %, 3 mL, ~10 eq.) followed by formic acid (1 mL) and the reaction mixture was stirred at room temperature overnight. Concentrated in vacuo to dryness to yield the crude product, which was directly used in the next step. Yield: 455 mg (98%) LCMS—[M+H] m/z 237.

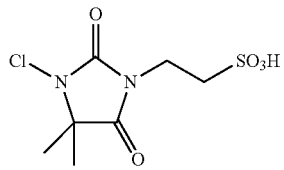 [SMILES: CC1(C)C(=O)N(CCS(=O)(=O)O)C(=O)N1Cl]

2-(3-Chloro-4,4-dimethyl-2,5-dioxoimidazolidin-1-yl)ethanesulfonic acid

To a portion of sulfonic acid (227 mg, 0.96 mmol, 1 eq.) in MeOH (5 mL) at 5° C. was added t-butylhypochlorite (207 mg, 1.92 mmol, 2 eq.) and the reaction was stirred for 2 h. Reaction was monitored by TLC and complete. Concentrated in vacuo and purified by column chromatography (gradient from 10% to 20% MeOH in DCM) to yield NVC-624 as a pure product. Yield: 102 mg (40%). $^1$H-NMR (400 MHz, CD$_3$OD-d$_4$ δ 3.97 (t, 2H), 3.13 (t, 2H), 1.45 (s, 6H). LCMS—[M−H] m/z 269.

Example 10

2-(1,8-Dichloro-7,7,9,9-tetramethyl-2,4-dioxo-1,3,8-triazaspiro[4.5]decan-3-yl)ethanesulfonic acid (Compound 22-25)

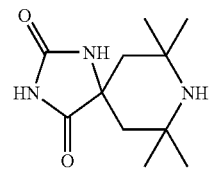

7,7,9,9-Tetramethyl-1,3,8-triazaspiro[4.5]decane-2,4-dione

Piperidone monohydrate (25 g, 163 mmol) and ammonium carbonate (34.5 g, 359 mmol) were suspended in a mixture of methanol (110 mL) and water (90 mL). To this suspension NaCN (17 g, 347 mmol) in water added dropwise. The reaction flask was sealed and heated at 50° C. for 48 h. Cooled and filtered and washed with small portions of water. Dried and concentrated to get the hydantoin (24 g, 87%). LCMS—[M+H] m/z 226.

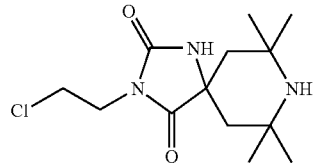 [SMILES: CC1(C)CC2(CC(C)(C)N1)NC(=O)N(CCCl)C2=O]

3-(2-Chloroethyl)-7,7,9,9-tetramethyl-1,3,8-triazaspiro[4.5]decane-2,4-dione

A mixture of 7,7,9,9-tetramethyl-1,3,8-triazaspiro[4.5]decane-2,4-dione (5, 22.2 mmol) and KOH (1.24 g, 22.2 mmol) in EtOH was refluxed for 10 min and bromochloroethane (6.35 g, 44.4 mmol) was added and refluxing continued for additional 6 h. Filtered and concentrated to get the crude chloroethylated product which was used as such for the next step (5.5 g). LCMS—[M+H] m/z 228.

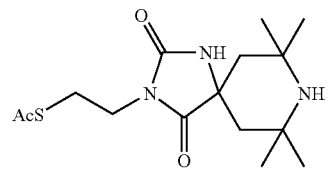

S-2-(7,7,9,9-Tetramethyl-2,4-dioxo-1,3,8-triazaspiro[4.5]decan-3-yl)ethyl ethanethioate 3-(2-Chloroethyl)-7,7,9,9-tetramethyl-1,3,8-triazaspiro[4.5]decane-2,4-dione (5.5 g. 19.2 mmol) and potassium thioacetate (4.37 g, 38.3 mmol) in DMF (30 mL) was heated at 80° C. overnight. Cooled to room temperature and filtered. Concentrated and purified over silica gel using 20% MeOH—CH$_2$Cl$_2$ to afford 3 g of the thioacetate. $^1$H NMR (CD$_3$OD, 400 MHz) δ 1.43 (s, 6H), 1.54 (s, 6H), 2.30 (s, 3H), 3.14-3.17 (m, 2H), 3.70-3.73 (m, 2H).

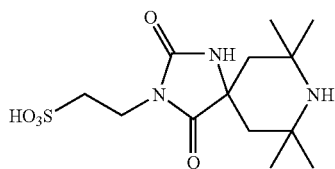 [SMILES: CC1(C)CC2(CC(C)(C)N1)NC(=O)N(CCS(=O)(=O)O)C2=O]

2-(7,7,9,9-Tetramethyl-2,4-dioxo-1,3,8-triazaspiro[4.5]decan-3-yl)ethanesulfonic acid S-2-(7,7,9,9-Tetramethyl-2,4-dioxo-1,3,8-triazaspiro[4.5]decan-3-yl)ethyl ethanethioate (3 g, 9.17 mmol) oxidized as before using performic acid to afford 2 g of the corresponding sulfonic acid. LCMS—[M+H] m/z 334.

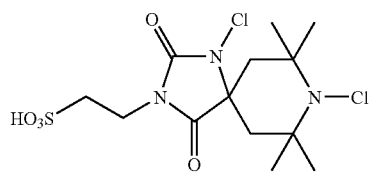 [SMILES: CC1(C)CC2(CC(C)(C)N1Cl)C(=O)N(CCS(=O)(=O)O)C(=O)N2Cl]

2-(1,8-Dichloro-7,7,9,9-tetramethyl-2,4-dioxo-1,3,8-triazaspiro[4.5]decan-3-yl)ethanesulfonic acid 2-(7,7,9,9-Tetramethyl-2,4-dioxo-1,3,8-triazaspiro[4.5]decan-3-yl)ethanesulfonic acid (0.5 g, 1.5 mmol) was chlorinated using HOCl as before to afford 500 mg of the dichloro compound. $^1$H NMR (D$_2$O, 400 MHz) δ 1.35 (s, 6H), 1.53 (s, 6H), 3.18-3.22 (m, 2H), 3.94-3.97 (m, 2H). LCMS—[M−H] m/z 400.

Example 11

2-(3-Chloro-4,4-dimethyl-2,5-dioxoimidazolidin-1-yl)-N,N,N-trimethylethanaminium chloride (Compound 22-48)

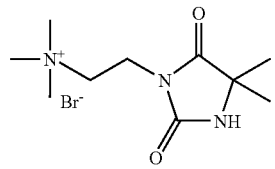

2-(4,4-Dimethyl-2,5-dioxoimidazolidin-1-yl)-N,N,N-trimethylethanaminium bromide

To a stirring solution of NaH (60% in mineral oil, 1.75 g) in DMF (25 mL) at 5° C. was added 5,5-dimethyl hydantoin (5 g, 39.0 mmol, 1 eq) and the reaction was stirred for 30 min. Added (2-bromoethyl)trimethylammonium (9.6 g, 39.0 mmol, 1 eq) at that temperature and the reaction was heated to 50° C., while stirring overnight. Reaction was cooled to room temperature and the product crashed out of solution as a white solid, which was cooled to 5° C., filtered and washed with cold DMF (30 mL). Purified by prep-HPLC (gradient from 5% to 95% MeOH in H$_2$O; 20 mL/min flow rate; C18 Restek column) to yield the desired product. Yield: 778 mg (7%). $^1$H-NMR (400 MHz, D$_2$O) δ 4.005 (t, J=7.6 Hz, 2H), 3.643 (t, J=7.6 Hz, 6H), 3.238 (s, 9H), 1.441 (s, 6H) LCMS—[M] m/z 214.05

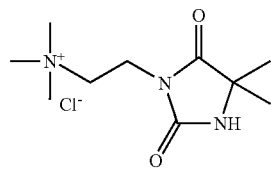

2-(4,4-Dimethyl-2,5-dioxoimidazolidin-1-yl)-N,N,N-trimethylethanaminium chloride To hydantoin bromide salt (778 mg, 2.65 mmol, 1 eq.) in H$_2$O (10 mL) and MeOH (10 mL) was added silver oxide (1.1 g, 4.76 mmol, 1.8 eq) in one portion to give a black suspension. Stirred for 1 h, and filtered through celite. The filtrate was acidified to pH 2 by adding 6 N HCl and this solution was filtered through celite, washing with H$_2$O (35 mL). The filtrate was concentrated to pale yellow oil. Yield: 341 mg (51%) LCMS—[M] m/z 214.05

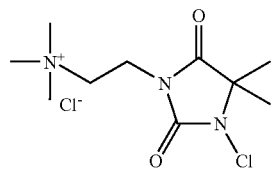

2-(3-Chloro-4,4-dimethyl-2,5-dioxoimidazolidin-1-yl)-N,N,N-trimethylethanaminium chloride To a portion of trimethyl ammonium hydantoin (250 mg, 1.00 mmol, 1 eq.) in MeOH (5 mL) at 5° C. was added t-BuOCl (500 mg, 4.62 mmol, 4.6 eq.) and the reaction was stirred for 1 h at 5° C. Concentrated in vacuo and purified by prep HPLC (gradient from 5% to 95% MeOH in $H_2O$; 20 mL/min flow rate; C18 Restek column) to yield NVC-668 as a pure product. Yield: 43 mg (15%). $^1$H-NMR (400 MHz, $D_2O$) δ 4.094 (t, J=6.8 Hz, 2H), 3.656 (t, J=7.2 Hz, 6H), 3.236 (s, 9H), 1.507 (s, 6H) LCMS—[M] m/z 248.05

Example 12

2-(3-Chloro-4,4-dimethyl-2-oxoimidazolidin-1-yl)-N,N,N-trimethylethanaminium acetate (Compound 22-49)

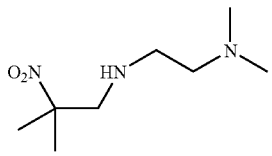

$N^1,N^1$-Dimethyl-$N^2$-(2-methyl-2-nitropropyl)ethane-1,2-diamine

To a solution of 2-nitropropane (2.07 g, 23.2 mmol) and $N^1,N^1$-dimethyl-ethane-1,2-diamine (2.22 g, 25.2 mmol) in 2-propanol (5 ml) was added 5 M NaOH in $H_2O$ (30 ul, 0.15 mmol), $H_2O$ (1 ml). 37% Formaldehyde in $H_2O$ (1.8 ml, 24 mmol) was added dropwise, and the reaction stirred for 22 h. The solution was concentrated in vacuo to half volume, acidified with sat. $NaHSO_4$ to pH 2, and washed with 3× 100 ml $CH_2Cl_2$. 15% NaOH in $H_2O$ was added to pH 12, and the slurry extracted with 3× 100 ml $CH_2Cl_2$. The organic phases were combined, dried on $MgSO_4$, concentrated in vacuo, and used without further purification. ESI/APCI (pos) expected for $C_8H_{19}N_3O_2$: 189.15. Found: 190 (MH$^+$).

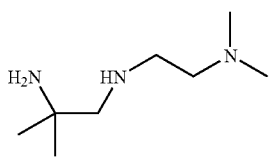

$N^1$-(2-(Dimethylamino)ethyl)-2-methylpropane-1,2-diamine

To a solution of $N^1,N^1$-dimethyl-$N^2$-(2-methyl-2-nitropropyl)ethane-1,2-diamine (23.2 mmol) in MeOH (20 ml) was added a slurry of Raney Nickel in $H_2O$ (1 ml). The vessel was pressurized with $H_2$ (500 psi) and the suspension stirred for 24 h. The mixture was filtered through Celite, then 0.45 um PTFE, and concentrated in vacuo. ESI/APCI (pos) expected for $C_8H_{21}N_3$: 159.17. Found: 160 (MH$^+$).

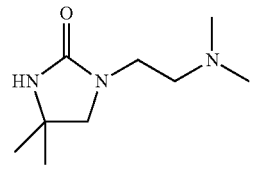

1-(2-(Dimethylamino)ethyl)-4,4-dimethylimidazolidin-2-one

To a solution of $N^1$-(2-(dimethylamino)ethyl)-2-methylpropane-1,2-diamine (23.2 mmol) in $CH_2Cl_2$ (50 ml) was added CDI (4.51 g, 27.8 mmol). The solution was stirred for 20 h, concentrated in vacuo, the resulting residue suspended in 800 ml diethyl ether, washed with 3× 200 ml 1M $Na_2CO_3$, 200 ml sat. NaCl, dried on $MgSO_4$, and concentrated in vacuo. Flash chromatography (2.5%→20% MeOH:$CH_2Cl_2$) afforded the title compound as a clear oil (79.3 mg, 0.428 mmol, 2%) as well as additional material heavily contaminated with imidazole g). $^1$H NMR (CDCl$_3$, 400 MHz) δ 1.24 (s, 6H), 2.23 (s, 6H), 2.41 (m, 2H), 3.24 (s, 2H), 3.34 (m, 2H), 4.96 (s, 1H). ESI/APCI (pos) expected for $C_9H_{19}N_3O$: 185.15. Found: 186 (MH$^+$).

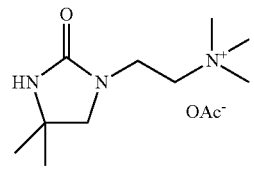

2-(4,4-Dimethyl-2-oxoimidazolidin-1-yl)-N,N,N-trimethylethanaminium acetate To a solution of 1-(2-(dimethylamino)ethyl)-4,4-dimethylimidazolidin-2-one (79.3 mg, 0.428 mmol) in MeOH (5 ml) was added methyl iodide (300 ul, 4.8 mmol). The solution was stirred for 18 h, concentrated in vacuo, dissolved in 2 ml $H_2O$, and $Ag_2O$ (300 mg, 1.2 mmol) and AcOH (200 ul, 2 mmol) was added. The suspension was stirred vigorously for 2 h, then filtered through 0.45 um PTFE. The solution was concentrated in vacuo and used without further purification. $^1$H-NMR ($D_2O$, 400 MHz) δ 1.18 (s, 6H), 1.84 (s, 3H), 3.09 (s, 9H), 3.24 (s, 2H), 3.43 (m, 2H), 3.56 (m, 2H). ESI/APCI (pos) expected for $C_{10}H_{22}N_3O^+$: 200.18. Found: 200.

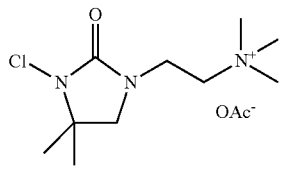

2-(3-Chloro-4,4-dimethyl-2-oxoimidazolidin-1-yl)-
N,N,N-trimethylethanaminium acetate A solution of 2-(4,4-dimethyl-2-oxoimidazolidin-1-yl)-N,N,N-trimethylethanaminium acetate (0.428 mmol) in MeOH (2 ml) was cooled to 0° C. tert-Butylhypochlorite (100 ul, 0.84 mmol) was added, causing a white precipitate to form. The solution was stirred for 15 min, and another portion of tert-butylhypochlorite (100 ul, 0.84 mmol) was added. The solution was stirred for an additional 15 min, then concentrated in vacuo. The residue was purified by RP-HPLC ($H_2O$/$CH_3CN$) to afford the title compound as a white powder (74.7 mg, 0.276 mmol, 65%). $^1$H NMR ($D_2O$, 400 MHz) δ 1.24 (s, 6H), 1.85 (s, 3H), 3.11 (s, 9H), 3.37 (s, 2H), 3.50 (m, 2H), 3.68 (m, 2H). $^{13}$C NMR ($D_2O$, 100 MHz) δ 22.32, 27.01, 39.24, 55.38, 57.82, 62.40, 161.31, 180.46. ESI/APCI (pos) expected for $C_{10}H_{21}ClN_3O^+$: 234.14. Found: 234.

Example 13

Antimicrobial Activity

To determine antimicrobial activity of compounds of the present disclosure, *Escherichia coli* (ATCC 25922), *Staphylococcus aureus* (ATCC 29213), *Pseudomonas aeruginosa* (ATCC 27853), and *Candida albicans* (ATCC 10231) were used in primary screening. In addition, *Escherichia coli* (MCC 80392), *Staphylococcus aureus* (MCC 91731), *Pseudomonas aeruginosa* (MCC 4438), and *Candida albicans* (MCC 50319), provided by Alcon Laboratories, Fort Worth, Tex., were used. The microbial cultures were diluted in sterile saline pH 4 to prepare inocula. Test compounds were titrated by stepwise two-fold dilutions in sterile saline pH 4. A total of $1.0\times10^5$ to $1.0\times10^6$ Colony Forming Units (CFU)/mL microbe was added to each tube, mixed by gentle vortexing, and then incubated at room temperature for 1 h. Microbial plating on Petri dishes (Tryptic Soy agar or Saboraud's Dextrose agar) was performed immediately after the designated exposure after neutralization of the test article dilutions in Dey-Engley Broth. Plates were incubated at 37° C., and the numbers of microbes were counted by direct colony count to quantitate the surviving microbes as CFU/mL. Positive growth controls were made with sterile 0.9% saline. Compounds were dissolved in unbuffered isotonic saline (SAL) or phosphate buffered saline (PBS) at pH 4 or pH 7 (using HCl and/or NaOH as needed). All compounds were tested three times. The results are tabulated to show the comparison of antimicrobial effectiveness range of the compounds.

Tables 2 and 3 show data obtained according to the method described above for selected compounds. Data shown are the Minimum Bactericidal Concentration (MBC) or Minimum Fungicidal Concentration (MFC) (≥99.9% kill) in µg/mL.

TABLE 3

| | E. coli MCC 80392 | | S. aureus MCC 91731 | | C. albicans MCC 50319 | |
|---|---|---|---|---|---|---|
| Cmpd | pH 4 (Sal) | pH 7 (PBS) | pH 4 (Sal) | pH 7 (PBS) | pH 4 (Sal) | pH 7 (PBS) |
| 22-01 | 2 | 16 | 16 | 16 | 128 | 128 |

Example 14

Cytotoxicity

Cytotoxicity is assessed by a colorimetric assay system using the Dojindo™ cell counting kit containing 2-(2-methoxy-4-nitrophenyl)-3-(4-nitrophenyl)-5-(2,4-disulfophenyl)-2H-tetrazolium, monosodium salt (WST-8). In this assay, the WST-8 reagent is bioreduced by cellular dehydrogenases to a formazan product that is highly soluble in tissue culture medium. The orange formazan, which is produced only by live cells, is a direct measure of cell viability and can be read spectrophotometrically (e.g., evaluation of a soluble tetrazolium/formazan assay for cell growth and drug sensitivity in culture using human and other tumor cell lines is described by D. A. Scudiero et al., *Cancer Res.*, 48(17), 4827-33 (1988). Similar approaches for determining the cell viability are known in the art.

In a standard assay, mouse fibroblast cells (ATCC CCL-1, L929), are cultured in Minimum Essential Medium, α-medium supplemented with 10% heat inactivated fetal bovine serum, L-glutamine, penicillin and streptomycin. Cells are trypsinized and counted under the microscope and seeded at $1.5\times10^4$ total cells per 100 µL per well of a flat-bottom 96-well plate in order to achieve ~80% confluence after overnight incubation at 37° C. On the day of the assay, the tissue culture medium is removed and replaced with 30 µL of fresh medium.

Test articles were prepared as 2-fold serial dilutions and 170 µL of each dilution was added into each of 4-wells (total volume per well=200 µL). The test plate was then returned to the 37° C. incubator for 60 min. Immediately after the exposed time, test article from each well was replaced with 200 µL of fresh media. Plates were incubated at 37° C. for 18-20 hours. The following day growth medium was replaced with 100 µL/well of fresh medium containing 10 µL WST-8 reagent. Cells were incubated under growth conditions (5% $CO_2$ at 37° C. humidified incubator), protected from light, until color development is achieved (usually 1-4 hours). Absorbance was read at 450 nm with reference wavelength at 750 nm using Molecular Device SpectraMax M5 plate reader.

TABLE 2

| | E. coli ATCC 25922 | | S. aureus ATCC 29213 | | C. albicans ATCC 10231 | | P. aeruginosa ATCC 27853 | |
|---|---|---|---|---|---|---|---|---|
| Cmpd | pH 4 (Sal) | pH 7 (PBS) | pH 4 (Sal) | pH 7 (PBS) | pH 4 (Sal) | pH 7 (PBS) | pH 4 (Sal) | pH 7 (PBS) |
| 22-01 | 256 | 128 | 256 | 256 | >512 | 1024 | * | 256 |
| 22-04 | 16 | * | 64 | * | >256 | * | * | * |
| 22-27 | 16 | * | 64 | * | >256 | * | * | * |
| 22-36 | 256 | 16 | 512 | 32 | * | 256 | * | * |
| 22-38 | 16 | 2 | 64 | 4 | * | 8 | * | * |
| 22-48 | 128 | 4 | >128 | 16 | 1024 | 128 | * | * |

* not tested

Untreated or vehicle only treated cells receiving WST-8 reagent served as positive cell proliferation controls.

Table 4 shows data ($CT_{50}$, in mM) obtained according to the method described above for selected compounds. The $CT_{50}$ value for each compound was calculated from the absorbance values ($A_{450/750}$) and is defined as the concentration of test article that results in survival of 50% of the cells following treatment. The absorbance $A_{450/750}$ from each well of untreated cells and from each well within the dilution series was measured. To calculate the $CT_{50}$ for each compound, all compound concentrations were first log-transformed using GraphPad Prism4 (version 4.03) software. Next, a non-linear regression (curve fit) analysis was performed on all the absorbance data measured from the dilution series, including the absorbance data obtained from wells of the untreated control cells. For each dilution within the dilution series, an average $A_{450/750}$ was calculated from the four replicate wells. The average $A_{450/750}$ data were plotted on a y-axis against the log-transformed compound concentration on the x-axis, and the $CT_{50}$ value calculated from the resulting best-fit curve.

TABLE 4

| Cmpd | pH 4 (Sal) |
| --- | --- |
| 22-01 | 1.1 |
| 22-36 | 0.7 |
| 22-38 | 0.86 |

While the foregoing description describes specific embodiments, those with ordinary skill in the art will appreciate that various modifications and alternatives can be developed. Accordingly, the particular embodiments described above are meant to be illustrative only, and not to limit the scope of the invention, which is to be given the full breadth of the appended claims, and any and all equivalents thereof.

What is claimed is:

1. A compound of Formula I

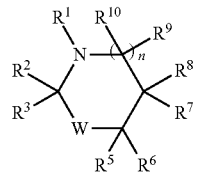

I or a salt thereof, wherein:
n is 0;
W is $NR^4$, or O;
$R^1$ is Cl, or Br;
$R^2$ and $R^3$ are each independently H, -L-X or optionally substituted alkyl or heteroalkyl or $R^2$ and $R^3$ together with the carbon to which they are attached form a carbonyl, or an optionally substituted cycloalkyl or heterocycloalkyl group;
$R^4$ is -L-X or optionally substituted alkyl or heteroalkyl;
$R^5$ and $R^6$ are each independently H, -L-X or optionally substituted alkyl or heteroalkyl; or $R^5$ and $R^6$ together with the carbon to which they are attached form a carbonyl, or an optionally substituted cycloalkyl or heterocycloalkyl group;
$R^7$ and $R^8$ are each independently H, -L-X or optionally substituted alkyl or heteroalkyl; or $R^7$ and $R^8$ together with the carbon to which they are attached form a carbonyl, or an optionally substituted cycloalkyl or heterocycloalkyl group;
each L is independently an optionally substituted $C_{1-6}$ alkyl, heteroalkyl, cycloalkyl or heterocycloalkyl group; and
each X is independently $-SO_3H$, $-N^+R^aR^bR^c$, $-CO_2H$, $-PO_3H_2$ or $-PO_3HR^a$ and $R^a$, $R^b$, and/or $R^c$ are independently a bond or an optionally substituted alkyl or heteroalkyl groups, or may form, together with the N to which they are attached, a heterocycloalkyl group
with the provisos that:
at least one of $R^2$, $R^3$, $R^4$, $R^5$, $R^6$, $R^7$, or $R^8$ is -L-X; and
one of $R^2$ and $R^3$, $R^5$ and $R^6$, or $R^7$ and $R^8$, together with the carbon to which they are attached, form a carbonyl.

2. The compound of claim 1, wherein the salt is a pharmaceutically acceptable salt.
3. The compound of claim 1, wherein W is O.
4. The compound of claim 1, wherein W is $NR^4$.
5. The compound of claim 1, wherein $R^1$ is Cl.
6. The compound of claim 1, wherein each L is a $C_{1-6}$ alkyl group.
7. The compound of claim 1, wherein X is $-SO_3H$ or $-N^+R^aR^bR^c$.
8. The compound of claim 1, wherein $R^a$, $R^b$ and $R^c$ are independently optionally substituted alkyl.
9. A compound of Formula IA

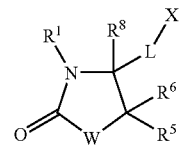

IA or a salt thereof, wherein:
W is $NR^4$ or O;
$R^1$ is Cl, or Br;
$R^4$ is H, Cl, Br or optionally substituted alkyl or heteroalkyl;
$R^5$ and $R^6$ are each independently H or optionally substituted alkyl or heteroalkyl; or an optionally substituted cycloalkyl or heterocycloalkyl;
$R^8$ is H, optionally substituted alkyl or heteroalkyl or -L-X;
each L is independently an optionally substituted $C_{1-6}$ alkyl, heteroalkyl, cycloalkyl or heterocycloalkyl group; and
each X is independently $-SO_3H$, $-N^+R^aR^bR^c$, $-CO_2H$, $-PO_3H_2$ or $-PO_3HR^a$ and $R^a$, $R^b$ and/or $R^c$ are independently and optionally substituted alkyl, heteroalkyl, groups, or may form, together with the N to which they are attached, a heterocycloalkyl group.

10. The compound of claim 9, wherein
$R^1$ is Cl;
W is O;
$R^5$ and $R^6$ are H or optionally substituted alkyl;
$R^8$ is H or optionally substituted alkyl,
L is a $C_{1-6}$ alkyl; and
X is $-SO_3H$, $-N^+R^aR^bR^c$ wherein $R^a$, $R^b$ and $R^c$ are independently an optionally substituted alkyl.

11. A compound selected from the group consisting of:
(3-chloro-4-methyl-2-oxooxazolidin-4-yl)methanesulfonic acid;

2-(3-chloro-4,4-dimethyl-2,5-dioxoimidazolidin-1-yl)
ethanesulfonic acid;
1-(3-chloro-1,4-dimethyl-2,5-dioxoimidazolidin-4-yl)-N,
N,N-trimethylmethanaminium chloride;
3-chloro-8,8-dimethyl-2-oxo-1-oxa-3-aza-8-azoniaspiro
[4.5]decane chloride;
1,3-dichloro-8,8-dimethyl-2,4-dioxo-1,3-diaza-8-azoniaspiro[4.5]decane;
N-((3-chloro-4-methyl-2-oxooxazolidin-4-yl)methyl)-N,
N-dimethylethanaminium chloride;
2-((3-Chloro-4-methyl-2-oxooxazolidin-4-yl)methylsulfonyl)ethanesulfonic acid;
N-((3-Chloro-4-methyl-2-oxooxazolidin-4-yl)methyl)-N,
N-dimethylpropan-1-aminium chloride;
2-(3-Chloro-4,4-dimethyl-2-oxoimidazolidin-1-yl)-N,N,
N-trimethylethanaminium acetate; and
a salt thereof.

12. A composition comprising a compound of claim 1 and a pharmaceutically acceptable carrier.

13. An antimicrobial composition comprising a compound of claim 1, formulated as an aerosol, cream, emulsion, gel, lotion, ointment, paste, powder, solid, solution, or suspension.

14. A method for treating a microbial ailment, condition or infection in a subject, comprising administering an effective amount of a compound of claim 1 to the subject.

15. A method of treating or preventing a microbial infection of skin or a mucous membrane comprising administering an effective amount of a compound of claim 1.

16. A method of treating or disinfecting a surface, comprising administering an effective amount of a compound of claim 1 to said surface.

17. The method of claim 16, wherein the surface is a surface of a medical device.

* * * * *